United States Patent
Tartz et al.

(10) Patent No.: US 10,349,212 B2
(45) Date of Patent: Jul. 9, 2019

(54) USING INTRABODY SIGNAL PROPAGATION TO INFER WEARABLE DEVICE LOCATION ON THE BODY FOR SENSOR OPTIMIZATION AND CONFIGURATION

(71) Applicant: QUALCOMM Incorporated, San Diego, CA (US)

(72) Inventors: Robert Scott Tartz, San Marcos, CA (US); Jay Steven King, San Diego, CA (US); Aniket Arun Vartak, San Diego, CA (US); Virginia Walker Keating, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 964 days.

(21) Appl. No.: 14/859,131

(22) Filed: Sep. 18, 2015

(65) Prior Publication Data
US 2017/0086023 A1    Mar. 23, 2017

(51) Int. Cl.
*A61B 5/00* (2006.01)
*A61B 5/01* (2006.01)
(Continued)

(52) U.S. Cl.
CPC .......... *H04W 4/023* (2013.01); *A61B 5/0028* (2013.01); *A61B 5/06* (2013.01); *H04B 1/38* (2013.01);
(Continued)

(58) Field of Classification Search
CPC .... H04W 4/023; H04M 1/72569; H04B 1/38; H04B 13/005; A61B 5/0028; A61B 5/06;
(Continued)

(56) References Cited

U.S. PATENT DOCUMENTS

| 8,867,994 B2 | 10/2014 | Kassayan | |
| 2006/0270915 A1* | 11/2006 | Ritter | A61B 5/026 600/300 |

(Continued)

FOREIGN PATENT DOCUMENTS

WO    WO-2009013708 A2    1/2009

OTHER PUBLICATIONS

Alomainy A., et al., "Parametric Study of Wearable Antennas with Varying Distances from the Body and Different on-Body Positions," IET Seminar on Antennas and Propagation for Body-Centric Wireless Communications, 2007, pp. 84-89.
(Continued)

*Primary Examiner* — Margaret G Mastrodonato
(74) *Attorney, Agent, or Firm* — Silicon Valley Patent Group LLP

(57) ABSTRACT

An electronic device is operated by determining its location on a body of a human or an animal, as an ending point of a path from another electronic device. The path is predetermined by measuring at multiple frequencies, a property indicative of loss of an AC signal that propagates through the body along the path between the pair of electronic devices, to obtain measurements. The multiple measurements are thereafter used to select a particular path through the body, from among a group of paths through the body which are characterized in one or more training phases, e.g. by use of a classifier. After a particular path through the body is identified, based on an ending point of the particular path, an electronic device at that ending point is configured, e.g. by turning on or turning off a specific sensor, or by setting a rate of transmission of data.

30 Claims, 15 Drawing Sheets

(51) Int. Cl.
*A61B 5/06* (2006.01)
*H04B 1/38* (2015.01)
*H04W 4/02* (2018.01)
*A61B 5/024* (2006.01)
*H04B 13/00* (2006.01)
*H04M 1/725* (2006.01)

(52) U.S. Cl.
CPC ...... *H04B 13/005* (2013.01); *H04M 1/72569* (2013.01); *A61B 5/01* (2013.01); *A61B 5/02416* (2013.01); *A61B 2562/0219* (2013.01)

(58) Field of Classification Search
CPC .................. A61B 5/01; A61B 5/02416; A61B 2562/0219
See application file for complete search history.

(56) References Cited

U.S. PATENT DOCUMENTS

| | | | |
|---|---|---|---|
| 2008/0262376 A1 | 10/2008 | Price | |
| 2011/0137133 A1* | 6/2011 | Espina Perez | G06F 19/3418 600/300 |
| 2011/0160801 A1* | 6/2011 | Markowitz | A61B 5/0028 607/60 |
| 2011/0269414 A1 | 11/2011 | Falck et al. | |
| 2012/0271143 A1 | 10/2012 | Aragones et al. | |
| 2016/0245766 A1* | 8/2016 | Nelson | G01N 27/023 |
| 2016/0278856 A1* | 9/2016 | Panescu | A61B 5/0422 |

OTHER PUBLICATIONS

Chandra R., et al., "A Link Loss Model for the on-Body Propagation Channel for Binaural Hearing Aids," IEEE Transactions on Antennas and Propagation, 2013, pp. 1-14.
Salman S., et al., "Pulmonary Edema Monitoring Sensor With Integrated Body-Area Network for Remote Medical Sensing," IEEE Transactions on Antennas and Propagation, May 2014, vol. 62 (5), pp. 2787-2794.
Seyedi M., et al., "A Survey on Intrabody Communications for Body Area Network Applications," IEEE Transactions on Biomedical Engineering, Aug. 2013, vol. 60 (8), pp. 2067-2079.
Sodani Y., et al., "Introduction of SVM into Personal Authentication Using Intra-Body Propagation Signals," IEEE Region 10 Conference TENCON, 2010, pp. 1617-1621.
Wang Z., et al., "Textile Antennas for Wearable Radio Frequency Applications," Textiles and Light Industrial Science and Technology (TLIST), Jul. 2013, vol. 2 (3), pp. 105-112.
Zimmerman T.G., "Personal Area Networks: Near-Field Intrabody Communication," IBM Systems Journal, 1996, vol. 35 (3 & 4), pp. 609-617.
Zimmerman T.G., "Personal Area Networks (PAN): Near-Field Intra-Body Communication," Massachusetts Institute of Technology, 1995, 81 pages.
Tamura T., et al., "Wearable Photoplethysmographic Sensors—Past and Present," Electronics 2014, ISSN 2079-9292, doi:10.3390/electronics3020282, pp. 282-302, Apr. 23, 2014.
"Appendix 1, S-parameter Basics," TDK Product Center, Technical Support, Technical Support Tools, SEAT 2013—SElection Assistant of TDK components Ver.5.2.1, Nov. 28, 2014, 11 pages, http://product.tdk.com/en/technicalsupport/seat/etutorial_007.pdf.
Mazloum N.S., "Body-Coupled Communications—Experimental characterization, channel modeling and physical layer design," Master Thesis, Ref. No. EX084/2008, Chalmers University of Technology, Department of Signals and Systems, Dec. 2008, 120 pages.
International Search Report and Written Opinion—PCT/US2016/047034—ISA/EPO—dated Nov. 4, 2016.
Meenupriya S., et al., "Optimization of Energy Efficient Relay Position for Galvanic Coupled Intra-body Communication," 2015 IEEE Wireless Communications and Networking Conference (WCNC), IEEE, Mar. 9, 2015 (Mar. 9, 2015), pp. 1725-1730, XP032786518, DOI: 10.1109/WCNC.2015.7127728 [retrieved on Jun. 17, 2015].

* cited by examiner

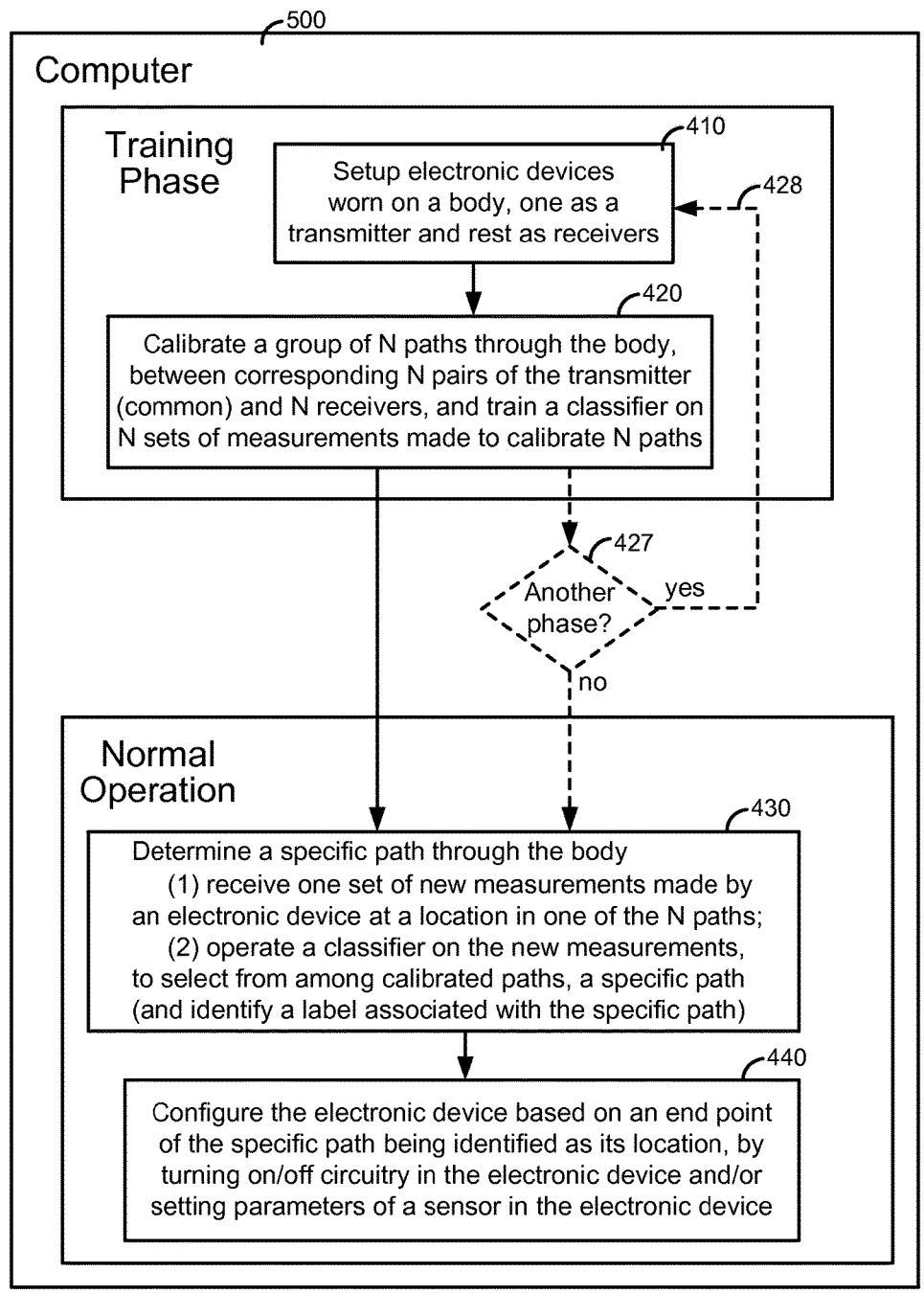

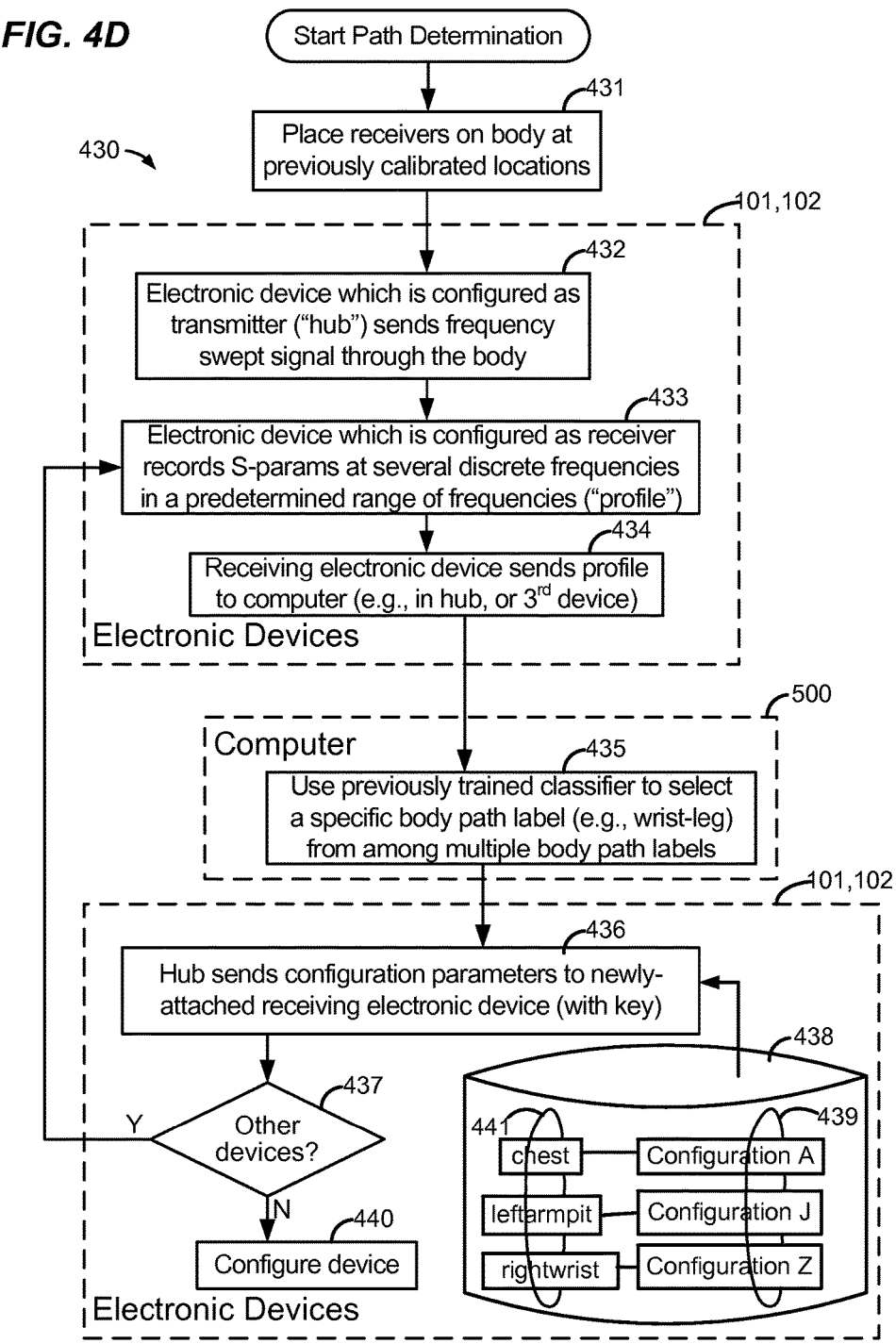

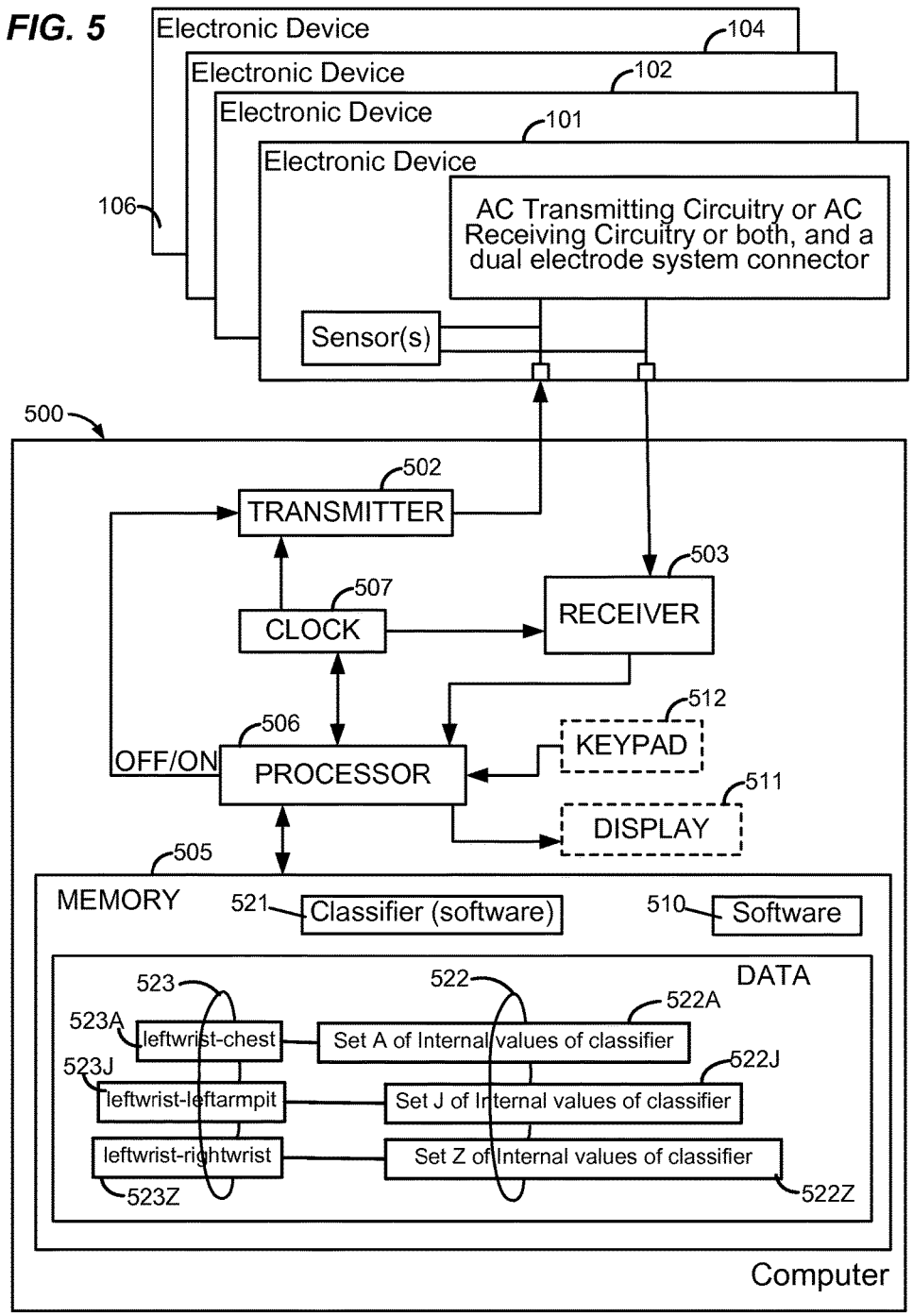

USING INTRABODY SIGNAL PROPAGATION TO INFER WEARABLE DEVICE LOCATION ON THE BODY FOR SENSOR OPTIMIZATION AND CONFIGURATION

BACKGROUND

This patent application relates to devices and methods for determining a location on a body at which an electronic device is worn by a human (or on an animal) and using the determined location to configure functionality and/or operational characteristic(s) of one or more of the electronic devices.

There are an increasing number of electronic devices that can be worn by users. Examples of such electronic devices include health/wellness monitoring (e.g., ECG monitors, Pulse oximeters), fitness applications (e.g., Nike+, Fitbit), head-mounted devices (e.g., Google glass), information displays (e.g., Qualcomm Toq) and entertainment applications. Other wearable devices could include electronic devices embedded into a ring, belt, pendant, hat, clothing or other objects commonly worn by humans on fingers, wrist, forearm, upper-arm, back of the ear, sternum, side, or ankle.

With the rapid evolution of wearable devices, electronic devices that collect multiple biosignals from a human body could be placed anywhere on the body. Contextually aware applications (e.g., a running smartphone app) can make use of the device/sensor location on a body for greater accuracy and power efficiency. There appears to be no known method of automatically identifying where on a human body, a device/sensor has been placed.

SUMMARY

In several aspects of described implementations, a sensor is configured and/or optimized based on inferring a location of the sensor on a body, using intrabody signal propagation. In intrabody signal propagation, an alternating current (AC) electrical signal passes through skin, tissue and organs of the body. Such implementations may determine a location (also called "receiving location"), at which an electronic device which includes the sensor receives an alternating current (AC) electrical signal, via intrabody signal propagation from another electronic device at another location (also called "transmitting location"), when both electronic devices are worn on a body of a human or animal.

A location of an electronic device on a body may be determined during normal operation by performing a first step of measuring the AC electrical signal at multiple frequencies, to obtain a set of measurements corresponding thereto of a specific attribute (e.g. amplitude or phase angle or both) of a scattering parameter (e.g. the scattering parameter $S_{21}$) of an electrical network formed by the two electronic devices with the body. A scattering parameter expresses characteristics of the electrical network using a degree of scattering, when the AC electrical signal passing through the body is considered as a wave. The degree of scattering indicates an amount of attenuation of the AC electrical signal propagating through the body ("intrabody signal propagation"), measured as the square root of electrical power. The set of measurements obtained in the first step of normal operation (which form a profile that corresponds to a specific pair of transmitting location and receiving location) may be used in a second step of normal operation, to select a receiving location from among N receiving locations on the body, which are characterized ahead of time (in one or more training phases, performed before normal operation).

In many implementations of the type described above, an AC signal is transmitted through the body by one electronic device (operable as an AC transmitter, also called "AC transmitting device") and received through the body by another electronic device (operable as an AC receiver, also called "AC receiving device"), which form in combination with the body, a two-port electrical network that is characterized by measurements of at least one scattering parameter of the AC signal at multiple frequencies. A set of measurements at the multiple frequencies (also called profile) that are made by an electronic device which is newly placed on the body are compared with profiles of a plurality of predetermined pairs of locations that are characterized ahead of time, to select therefrom a particular predetermined pair of locations (within which a receiving location is where the electronic device is newly placed). The particular predetermined pair of locations is selected based on each profile having been associated with a corresponding pair of locations (in the plurality of predetermined pairs of locations) during training. For example, such a selection is done automatically in some implementations by use of a classifier to select the particular predetermined pair of locations (which includes therein a receiving location at which the electronic device is located) from among the plurality of predetermined pairs of locations on the body. The classifier is trained ahead of normal operation, by use of sets of additional measurements (or profiles) to predetermine a plurality of pairs of locations, wherein each set of these additional measurements (or profile) is obtained by similarly propagating an AC electrical signal between each pair among the plurality of pairs of locations, from among which a selection of a particular pair is to be made during normal operation.

In some implementations, each predetermined pair in a group of predetermined pairs of body locations has a transmitting location in common with another predetermined pair in the group of predetermined pairs of body locations, and the just-described transmitting location is predetermined on the body (e.g. left wrist). In certain implementations, an AC transmitting device is attached at any known location (e.g. left wrist) that may form a common starting point for an AC electrical signal. The AC electrical signal transmitted at the known location may be received at two or more predetermined receiving location(s) through the body, and each of these two or more predetermined receiving location(s) is paired with the known location, to form a corresponding pair in the group of pairs. Accordingly, depending on the implementation, an AC receiving device may be automatically configured, by identification of a particular predetermined pair of locations (also called particular path) that is determined by selection from among a group of predetermined pairs of locations (or paths), by use of a new set of AC signal measurements (or profile) that uniquely identifies the particular predetermined pair of locations (or particular path) among the group, with each predetermined pair of locations in the group including the known location (e.g. left wrist) as a common starting point.

Characterization of a plurality of paths (or a plurality of pairs of locations), in one or more phases of training, may be performed in some implementations as follows. When an electronic device is first placed on a body at any location, AC transmitting circuitry within this first-placed electronic device is enabled, and any electronic devices that are later placed on the body at any other locations have their AC transmitting circuitry disabled initially although their AC receiving circuitry is enabled initially. In some implementations, user input is received (e.g. via a touchpad), to label a body location of each electronic device, e.g. a string of characters "leftwrist" may be received to identify the location of the first-placed electronic device. During a phase of training, each of one or more later-placed electronic devices obtain a corresponding set of measurements (or profiles) of an AC electrical signal transmitted by the first-placed electronic device. In such implementations, user input is additionally received (e.g. via the touchpad), to label each of the locations of the later-placed electronic devices (e.g. the strings of characters "chest", "leftarmpit", "lefthandmiddlefinger" and "rightwrist" may be received). At the end of the just-described training phase, N sets of measurements (or N profiles) are internally associated by a classifier with N labels of the N pairs of locations of one or more later-placed electronic device(s) relative to the first-placed electronic device (thus, these N pairs of locations are now predetermined).

In some implementations (called single-training-phase implementations), when the training phase is completed, one or more later-placed electronic devices may be removed from the body. A first-placed electronic device may continue to be worn on the body at the same location (which is a common starting point for the AC electrical signal) during normal operation as its original location during the training phase. When an electronic device is again worn on the body during normal operation at a particular location among the N locations, the electronic device now generates a new set of measurements of the AC electrical signal (which is transmitted by the first-placed electronic device, at the common starting point). The classifier receives the new set of measurements and in a second step of normal operation (described above) uses its internal values (generated during the training phase, based on the N sets of measurements or N profiles) to automatically select from among N labels of the N locations (or corresponding N paths each including a location of the common starting point), the label of the particular location at which the electronic device that generated the new set of measurements has been worn on the body (after the training phase). The particular location's label is then used, to configure sensors inside this electronic device.

In certain implementations (called multiple-training-phase implementations), each electronic device may be iteratively operated as an AC transmitter, and the rest of the electronic devices may be operated as AC receivers. Specifically, in several such implementations, the above-described training phase may be repeated M times as follows. The first-placed electronic device has its AC transmitting circuitry disabled, and during each of M−1 iterations after the first iteration, AC transmitting circuitry is enabled in a different later-placed electronic device, thereby to characterize M−1 groups of pairs of body locations, in M−1 corresponding phases of training. In each of the M phases (i.e. during each of the M iterations), one group of pairs of locations individually contains a known location (or starting point) which is common to all pairs of locations (or paths) in that one group. Measurements in each of the M−1 phases of training may be made selectively, to characterize only a group of new pairs of locations, wherein each combination of locations in a new pair did not exist in an earlier phase of training (e.g. based on use of a new known location for a new starting point).

In several implementations, during normal operation, a predetermined pair of locations (or predetermined path) is automatically determined, by measuring in a newly-placed electronic device, a profile of an AC electrical signal transmitted by an earlier-placed electronic device, and using the measured profile with a classifier to select a specific path from among multiple paths that have been characterized during one or more training phases, by use of one or more groups of profiles. Then, a particular location on the body of the newly-placed electronic device is automatically identified, as the ending point of the specific path (or a receiving location in the predetermined pair of locations) selected by the classifier. After the particular location of the newly-placed electronic device is identified in normal operation as just described, based thereon one or more sensor(s) within the newly-placed electronic device may be automatically configured.

In a first example of sensor configuration, a circuit is turned on or off in a newly-placed electronic device, depending on a location identified for the newly-placed electronic device. More specifically, a sensor in the form of a pulse rate monitoring circuit may be turned off to reduce power consumption, when a particular location of this newly-placed electronic device is identified, in the second step of normal operation described above, to be on a specific body part (e.g. an ankle) from which a signal measured by the sensor (e.g. pulse rate) is unnecessary. A second example of configuration turns on or turns off collection of data of a particular type from the newly-placed electronic device, based on this newly-placed electronic device's particular location on the body. In a third example of configuration, operational characteristics are configured, by setting a specific rate of transmission of data to or from a newly-placed electronic device to optimize power consumption, based on this newly-placed electronic device's particular location on the body. In a fourth example of configuration, performance of a newly-placed electronic device may be optimized by dynamically adjusting thresholds, e.g. setting a threshold for counting a step in an activity sensor based on its particular location on the body, because counting a step in this electronic device when worn on a leg requires a different threshold for a sensor therein than counting a step by the sensor in this same electronic device when worn on the waist.

A method of the type described above is used in some implementations, by a generic wearable electronic device which contains multiple sensors (e.g. accelerometer, temperature sensor, photoplethysmography (PPG) sensor etc), and further contains AC transmitting circuitry to transmit an AC electrical signal, AC receiving circuitry to measure the AC electrical signal, and a computer to use these measurements with a classifier therein to automatically identify its location on a body (relative to another such electronic device), and to then use the identified relative location to automatically configure at least one of one or more multiple sensors therein, to measure a specific property of the body.

It is to be understood that several other aspects of the invention will become readily apparent to those skilled in the art from the description herein, wherein it is shown and described various aspects by way of illustration. The drawings and detailed description below are to be regarded as illustrative in nature and not as restrictive.

BRIEF DESCRIPTION OF DRAWINGS

FIG. 4A illustrates, in a flow chart, acts performed in some implementations, to determine and use a predetermined path through body 100 that denotes a predetermined pair of locations, to configure AC transmitting and receiving devices of the type illustrated in FIGS. 1A-1B, 2A-2D, and 3A-3C.

FIG. 4D illustrates, in still another flow chart, acts performed in some implementations, in a path-determination operation 430 in FIG. 4C.

FIG. 5 illustrates, illustrates, in a high-level block diagram, various components of electronic devices 101, 102, 104 and 106, in some of the described implementations.

DETAILED DESCRIPTION

Figure 1A:
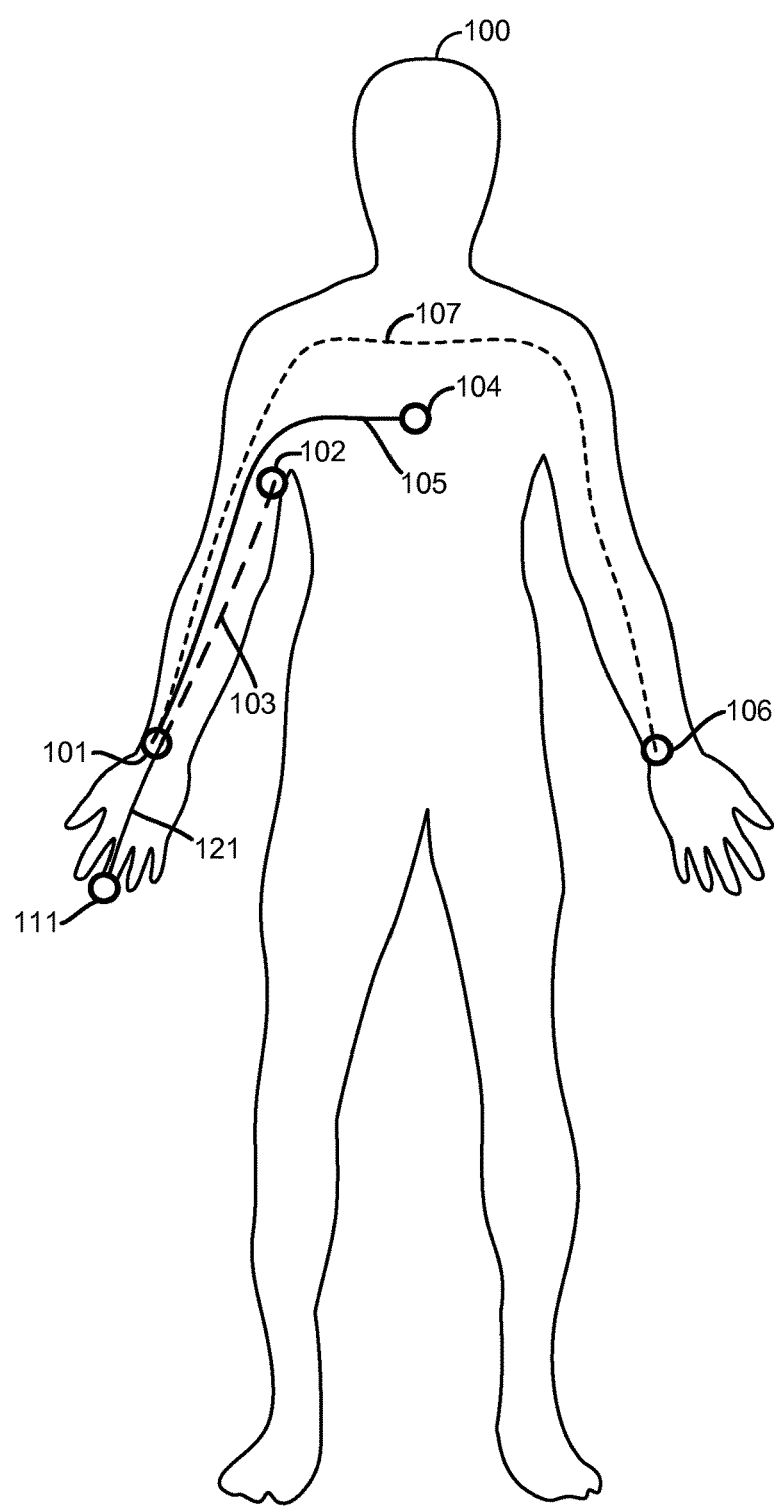
FIG. 1A illustrates paths 103, 105, 107 and 121 that denote corresponding predetermined pairs of locations of electronic devices (specifically an AC transmitting device and an AC receiving device), namely locations of device pairs (101, 102), (101, 104), (101, 106), and (101, 111) worn on a body 100 of a human (or an animal), in several aspects of described implementations.

In several aspects of described implementations, a location on a body 100 (FIG. 1A) of a living human (or animal) may be determined as an ending point of a predetermined path that denotes a predetermined pair of locations, namely one location of an electronic device operable at least as an AC transmitting device, and another location of an electronic device operable at least as an AC receiving device. For example, a predetermined path 103 denotes a predetermined pair of locations of electronic devices 101 and 102, another predetermined path 105 denotes a predetermined pair of locations of electronic devices 101 and 104, still another predetermined path 107 denotes a predetermined pair of locations of electronic devices 101 and 106, and yet another predetermined path 121 denotes a predetermined pair of locations of electronic devices 101 and 111.

In some implementations, an electronic device 101 (which contains AC transmitting circuitry and is operable as an AC transmitting device) may be worn at a predetermined location on body 100, e.g. on a wrist of an arm, such as the wrist of the left arm. The same electronic device 101, which may additionally contain AC receiving circuitry and be additionally operable as an AC receiving device, may alternatively be worn at a different predetermined location on body 100, e.g. electronic device 101 may be worn in other implementations, at other locations such as head, upper arm, or chest. Hence, electronic devices 101, 102, 104, 106 or 111 which are operable as an AC transmitting device and/or an AC receiving device can take any form, such as a headset, a watch, a necklace, an armband, or a chest-strap. In some implementations, a known location on body 100 (e.g. left wrist) forms a single starting point of an AC signal (also called "transmitting location"). In such implementations, the starting point is common to a group of paths (or group of pairs of locations). In several such implementations, each predetermined pair of locations (denoted by a path) in a group includes a known location of an electronic device 101 and one of multiple predetermined locations of additional electronic devices 102, 104, and 106 ("receiving locations").

A particular location at which one of electronic devices 102, 104, 106 or 111 (FIG. 1A) is newly worn on body 100 may be automatically identified during normal operation of certain implementations as follows: (1) in a first step, measure at multiple frequencies, a property of an alternating current (AC) electrical signal that propagates from a starting point on body 100 through skin, tissue and organs in body 100 through an intrabody path between the pair of electronic devices (such as electronic devices 101, and 102), to obtain a set of multiple measurements (or a profile) at one of the electronic devices (such as electronic device 102), and (2) in a second step, use the multiple measurements (or profile) to determine a particular path (such as path 103) through body 100, and thereby determine a receiving location at an end of that particular path.

In the second step described above, the particular path's receiving location is determined during the normal operation of such implementations e.g. by use of a classifier which is trained ahead of time, to automatically select (and thereby automatically identify) the particular path from among a group of paths. A group of paths may include e.g. paths 103, 105, 107 and 121 denoting the single transmitting location of electronic device 101 (which constitutes a starting point) and the different receiving locations of electronic devices 102, 104, 106, or 111 (FIG. 1A) (which constitute different ending points of respective paths 103, 105, 107, and 121 along which an AC electrical signal propagates). Such a classifier (e.g. implemented as a neural network) may be trained ahead of time (i.e. prior to normal operation), in one or more training phases, by use of electronic device 101 attached to the body at the common predetermined location (or starting point) as an AC transmitting device, to generate and transmit an AC electrical signal at a frequency that changes over time (e.g. in a predetermined manner, or as per external input), and making measurements at different frequencies to form a profile at each of the other predetermined locations (or ending points) by the electronic devices 102, 104, 106 or 111 (FIG. 1A), and using the profile of each path (between the starting point and one of the ending points) in training.

Certain implementations (called single-training-phase implementations) use only one starting point (e.g. left wrist location of electronic device 101 in FIG. 1D) for all paths that are characterized ahead of time in one training phase. Other implementations (called multiple-training-phase implementations) may use multiple starting points. For example, a left wrist location of electronic device 101 is used in a first training phase, followed by use of chest location of electronic device 104 in FIG. 1D in a second training phase, to characterize multiple groups of paths (e.g. two groups of paths), wherein each group of paths individually contains a single starting point for all paths in said each group (e.g. first group of paths starting at electronic device 101 in FIG. 1A, second group of paths starting at electronic device 104 in FIG. 1E).

In some multiple-training-phase implementations, an electronic device 101 (FIG. 1A) which is first placed on body 100 may be initially operated in a first training phase as an AC transmitting device located at a first starting point (e.g. left wrist location of electronic device 101) while other electronic devices ("later-placed electronic devices") later placed on body 100 at several first ending points (e.g. location of electronic device 104 on the chest, location of electronic device 102 on the left ankle, location of electronic device 120 on an index finger of the right hand, location of electronic device 108 on the right ankle in FIG. 1D) measure a frequency-swept AC signal ("first AC signal") originating at the first starting point, to form a first group of measurement profiles. This first group of measurement profiles characterizes a first group of paths, between the just-described first starting point (at a common known location, e.g. left wrist) and the first ending points.

Depending on the implementation, a first training phase of the type described above may be followed by additional training phases in which is operated an AC transmitting device at other known locations (e.g. chest) on body 100, to obtain additional groups of measurement profiles to characterize additional groups of paths. Specifically, in a second training phase, electronic device 104 (FIG. 1E) that contains AC signal transmitting circuitry (which was kept unused in the first training phase), and which is located at one of the just-described first ending points (e.g. chest), hereinafter a second starting point, may be used as the AC transmitting device to obtain a group of additional measurement profiles, e.g. to characterize the paths 141, 142 and 143 from electronic device 104 at a second starting point, to corresponding electronic devices 111, 102 and 106 as shown in FIG. 1E.

Figure 4B:
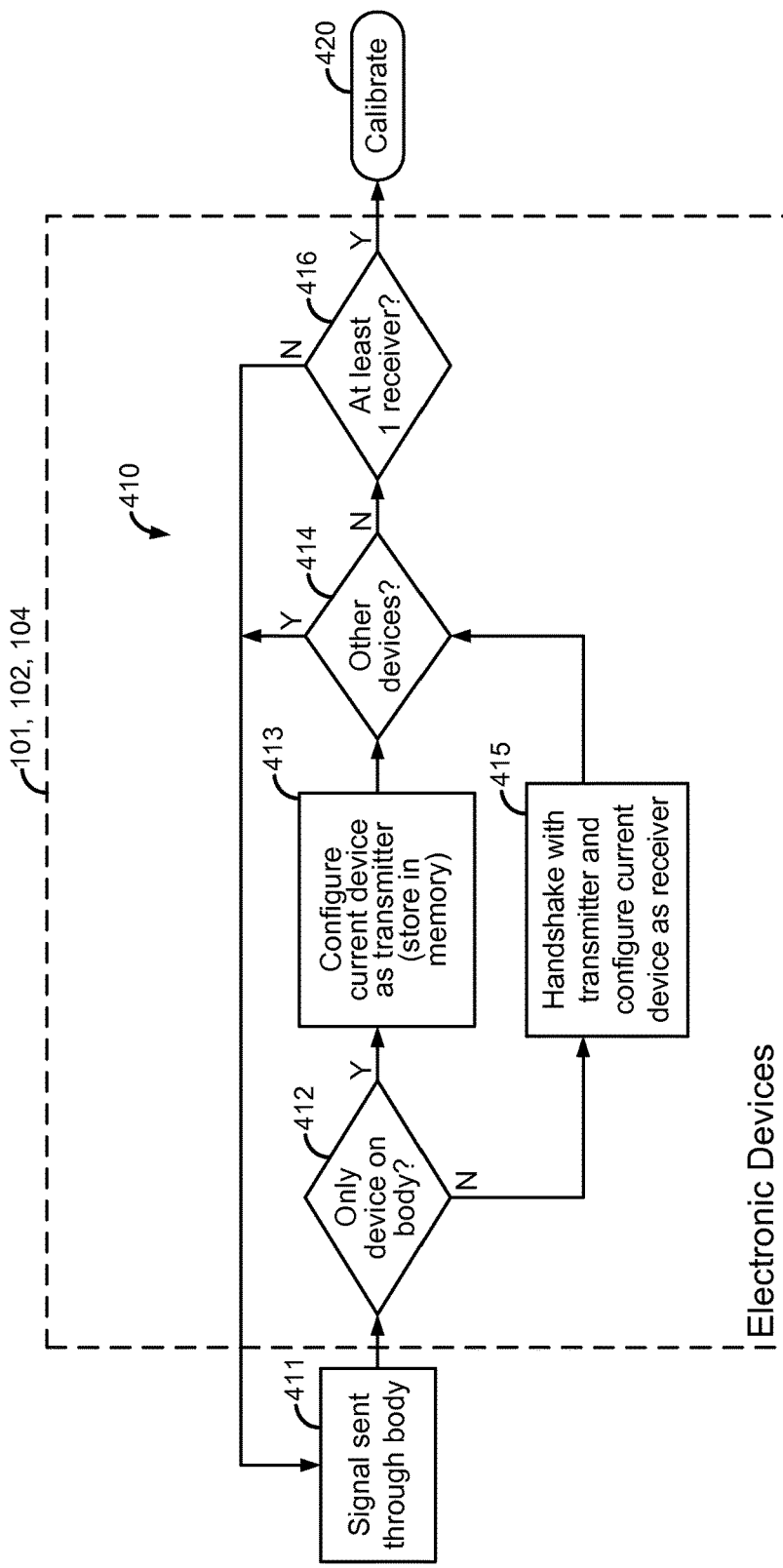
FIG. 4B illustrates, in a flow chart, acts performed by a computer 500 in some implementations, in a setup operation 410 in FIG. 4A.

In some alternative implementations, only one of the electronic devices contains AC signal transmitting circuitry, and thus during the second training phase, the first-placed electronic device, e.g. electronic device 101 (FIG. 1A) may be manually moved to another known location (e.g. chest) on body 100 for use as the AC transmitting device. During this second training phase, the above-described electronic devices 111, 102 and 106 located at the remainder of the above-described first ending points (e.g. at the left hand finger, at the left arm pit, and at the right wrist), hereinafter second ending points, measure the frequency-swept AC signal ("second AC signal") originating at the second starting point, to form a second group of measurement profiles that characterize a new group of paths (e.g. paths 141, 142 and 143) not previously characterized, specifically between a second starting point (e.g. on the chest) and one or more second ending points (e.g. at the left hand finger, at the left arm pit, and at the right wrist in FIG. 1E). In this manner, multiple-training-phase implementations may iterate over several starting points (e.g. as shown by branch 428 in FIG. 4A), to perform several training phases corresponding to several groups of paths, thereby to associate a specific profile with a specific path in each group of paths (e.g. by storing in memory internal values of a classifier, based on measurements in the training phases).

All electronic devices 101, 102, 104, 106 and 111 (FIG. 1A) described above include at least circuitry to receive and measure an AC electrical signal (also called AC signal receiving circuitry, or simply AC receiving circuitry). In implementations of electronic devices that are generic, each of electronic devices 101, 102, 104, 106 and 111 additionally contains circuitry to transmit the AC electrical signal (also called AC signal transmitting circuitry, or simply AC transmitting circuitry). In such implementations, whichever one of the electronic devices 101, 102, 104, 106 and 111 happens to be placed on a body 100 first in time ("first-placed" device) is automatically operated as an AC transmitting device (e.g. electronic device 101 in FIG. 1A) in a first training phase, while the AC signal transmitting circuitry in other electronic devices ("later-placed" devices) is disabled (or before later-placed devices are placed on body 100). This first training phase is followed by operation of AC signal transmitting circuitry to transmit a second AC electrical signal from a later-placed device (e.g. electronic device 104 on the chest in FIG. 1E) in a subsequent training phase, while turning off or disabling at least the AC signal transmitting circuitry in the first-placed device (e.g. electronic device 101, already used in the first training phase).

In some alternative implementations (called uni-transmitter implementations) only one of the electronic devices worn on a body 100 includes circuitry to transmit the AC electrical signal (e.g. electronic device 101 in FIG. 1A). In uni-transmitter implementations, two or more groups of paths of the type described above may be characterized ahead of time, by a human user manually moving the single electronic device (e.g. electronic device 101) which contains circuitry to transmit the AC electrical signal, from the above-described first starting point (e.g. left wrist) to other starting points (e.g. chest, right wrist) on body 100.

During the normal operation, based on an identity of the particular path (e.g. path 103 in FIG. 1A) that has been determined (and optionally based on identity of a common predetermined location of electronic device 101 operable as an AC transmitting device, depending on the implementation), a specific other predetermined location of electronic device 102 (which is operable at least as an AC receiving device) is automatically identified, followed by automatic configuration of electronic device 102. Automatic configuration of a newly-placed electronic device based on its body location eliminates user input otherwise needed during normal operation, to identify where on body 100 is the electronic device 102 (operable at least as an AC receiving device).

A property which is being measured as described above, in one or more measurements, is indicative of loss of the AC signal at least due to scattering during propagation through body 100, and the property depends on a frequency at which the AC signal oscillates. The property which is measured at multiple frequencies is different in different implementations, and some implementations measure one or more attributes (e.g. amplitude or phase angle), of one of four scattering parameters also called S-parameters, such as $S_{11}$, $S_{12}$, $S_{21}$, or $S_{22}$. Any one of these S-parameters may be used depending on the implementation, and specifically some illustrative implementations use the scattering parameter $S_{21}$, by measuring either or both of two attributes thereof, namely amplitude and/or phase angle, as shown in FIGS. 1B and 1C.

Figure 1B:
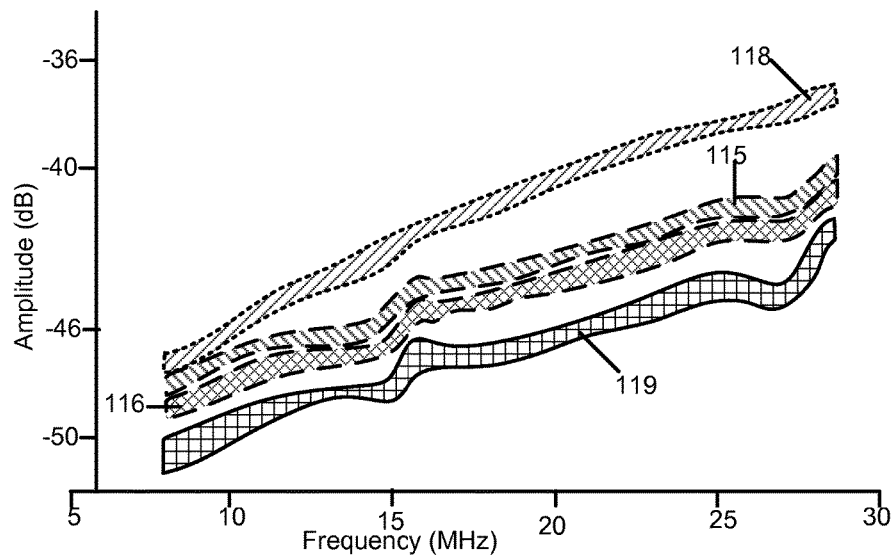
FIG. 1B illustrates, in a graph, several $S_{21}$ amplitude profiles of various paths through body 100 of FIG. 1A between corresponding predetermined pairs of locations as a function of frequency.

Specifically, FIG. 1B illustrates a profile 115 containing a set of amplitude measurements of the scattering parameter $S_{21}$ as a function of frequency, which are measured prior to normal operation for an intrabody AC electrical signal that propagates along a path 105 (FIG. 1A) from electronic device 101 (operable as an AC transmitting device) to electronic device 104 (operable as an AC transmitting device) that are respectively located on a left wrist and chest (sternum) of body 100. And, FIG. 1C illustrates another profile 125 containing a set of phase angle measurements of the scattering parameter $S_{21}$ as a function of frequency for the just-described intrabody AC electrical signal propagating along path 105 (FIG. 1A) between electronic devices 101 and 104. FIG. 1B illustrates other profiles containing other sets of amplitude measurements of the scattering parameter $S_{21}$ measured for other intrabody AC electrical signals propagating along other paths as shown in the following table, with each path originating at the same location, namely the left wrist:

| | |
|---|---|
| Profile 118 | For a path 121 (FIG. 1A) ending at a finger of the left hand of body 100 (at which electronic device 111 is located) |
| Profile 116 | For path 107 (FIG. 1A) ending at a right wrist of body 100 |
| Profile 119 | For path 103 (FIG. 1A) ending at upper part of left arm of body 100 |

Figure 1C:
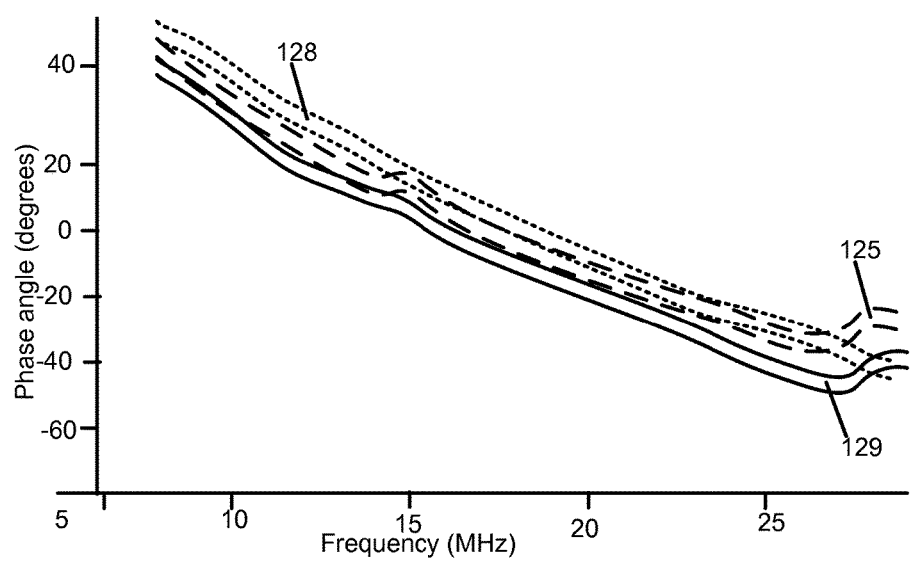
FIG. 1C illustrates, in another graph, several $S_{21}$ phase angle profiles of various paths through body 100 of FIG. 1A between corresponding predetermined pairs of locations as a function of frequency.

Moreover, FIG. 1C illustrates other profiles containing other sets of phase angle measurements for other intrabody AC electrical signals propagating along other paths originating at the left wrist, as shown in the following table:

| | |
|---|---|
| Profile 128 | For path 121 ending at finger of the left hand of body 100 (at which electronic device 111 is located) |
| Profile 129 | For path 103 (FIG. 1A) ending at upper part of left arm of body 100 |

Figure 1D:
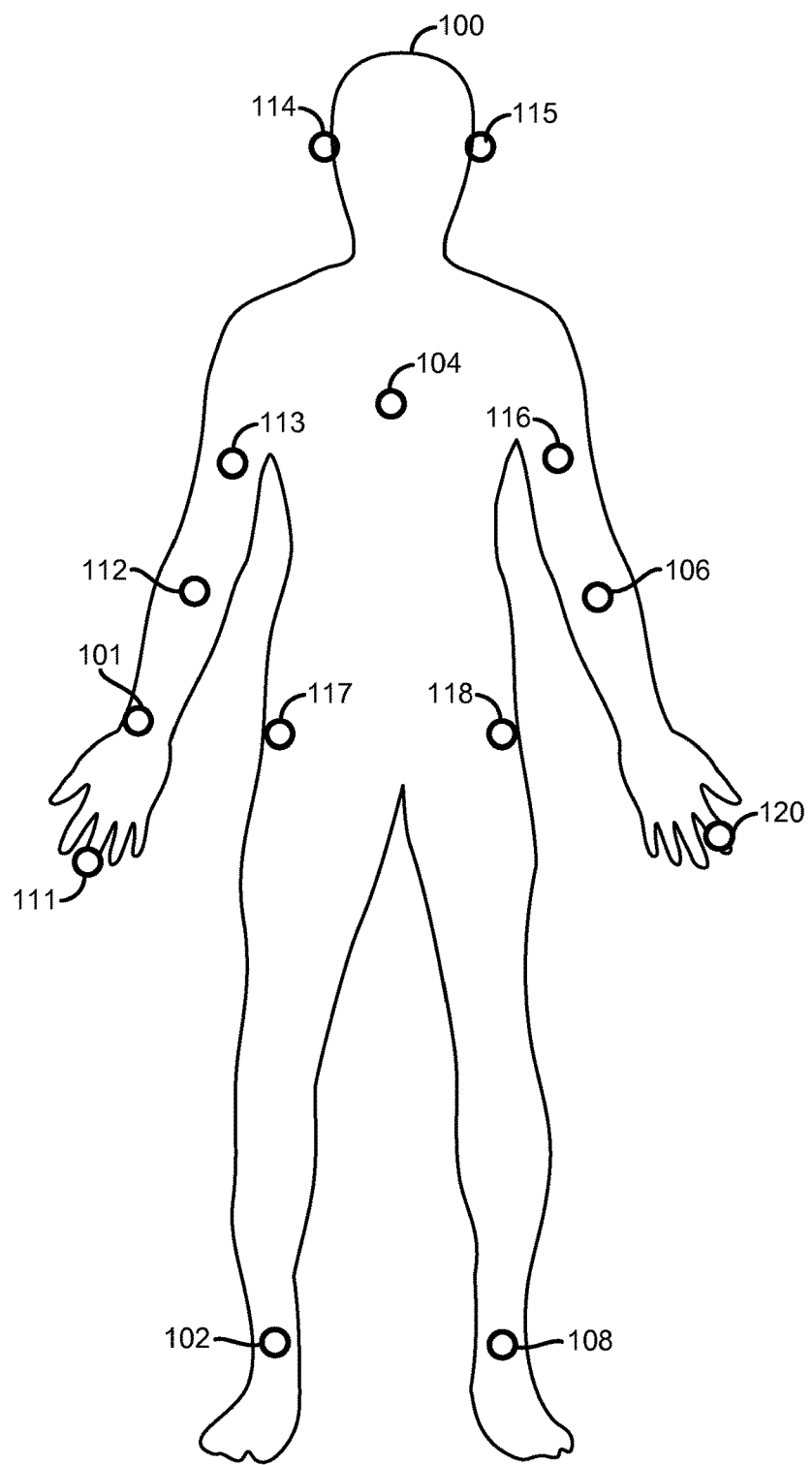
FIG. 1D illustrates AC receiving electronic devices 111-120 also worn on body 100 of FIG. 1A in addition to one AC transmitting device 101, and multiple AC receiving devices 102, 104 and 106, in certain aspects of described implementations.
Figure 1E:
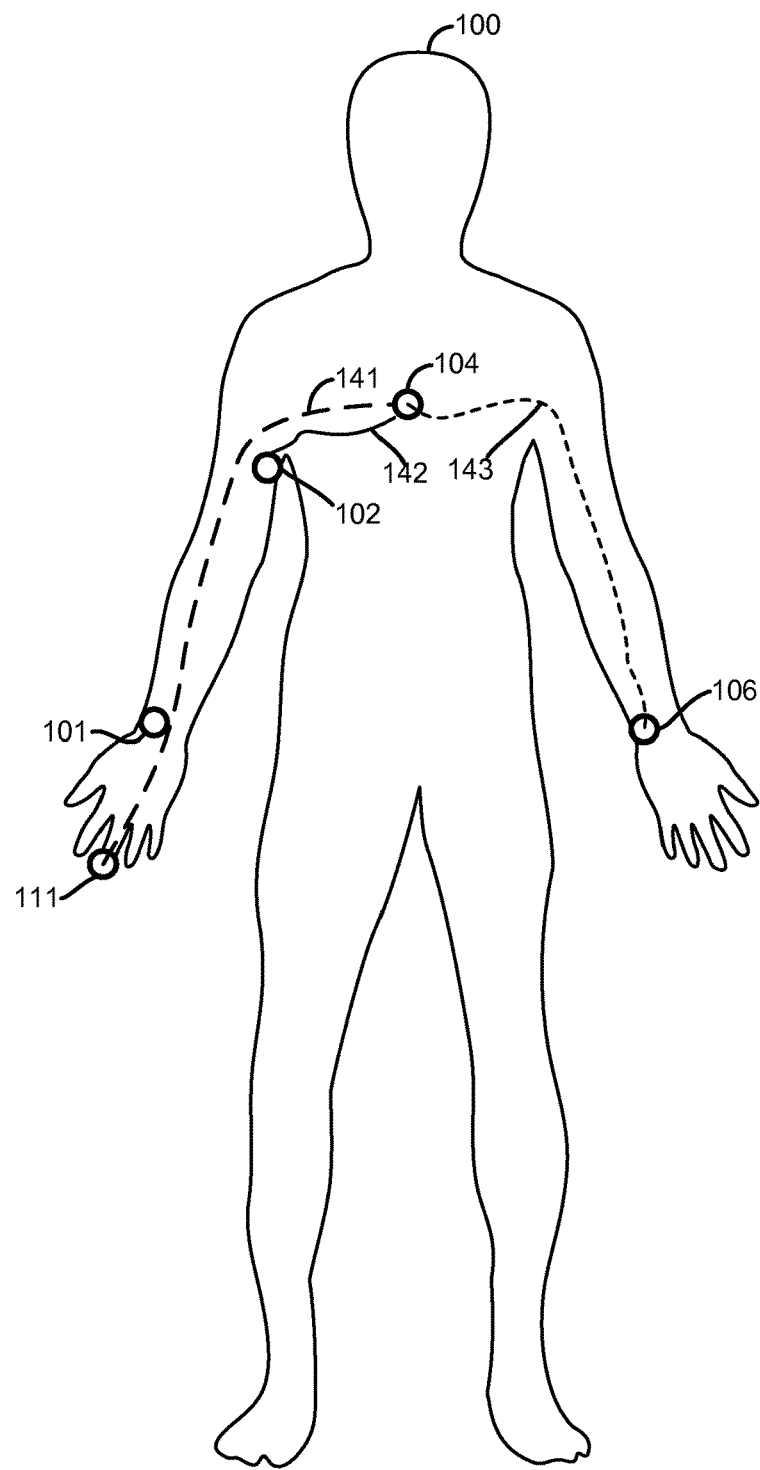
FIG. 1E illustrates paths 141, 142, and 143 that denote corresponding predetermined pairs of locations of electronic devices (specifically an AC transmitting device and an AC receiving device), namely locations of device pairs (104, 111), (104, 102), and (104, 106), worn on a body 100 of a human (or an animal), in several aspects of described implementations.

Specifically, in some implementations of the type illustrated in FIG. 1D, electronic devices 111-120 (which are operable as AC receiving devices) may be worn simultaneously at several other predetermined locations on body 100 of FIG. 1A in addition to electronic devices 101, 102, 104 and 106, in certain aspects of described implementations, and paths corresponding thereto are characterized by bands of the type illustrated in FIGS. 1B and 1C, which are used to train the classifier in the training phase, prior to normal operation. During the training phase, each of the bands may be associated, based on user input, with a label 523J (FIG. 5) of a path. In some implementations, each path may be labeled based on both its starting point and ending point, e.g. label 523Z (FIG. 5) of value "leftwrist-rightwrist" for path 107 (FIG. 1A), label 523A (FIG. 5) of value "leftwrist-chest" for path 105 (FIG. 1A), and label 523J (FIG. 5) of value "leftwrist-leftarmpit" for path 103 (FIG. 1A). In other implementations (e.g. single-training-phase implementations), each path may be labeled based on only the ending point, when the starting point is at a common known location (e.g. label of value "leftwrist" is known), by using labels 441 (FIG. 4D), such as label of value "rightwrist" for path 107 (FIG. 1A), label of value "chest" for path 105 (FIG. 1A), and label of value "leftarmpit" for path 103 (FIG. 1A).

During normal operation, an identifier of a particular path 103 is determined by use of classifier 521 (FIG. 5), based on a set of multiple measurements at multiple frequencies (which form a profile), the set of measurements being made in an electronic device 102. Classifier 521 stores in memory 505 internal values 522 that are derived from previously being trained on past data, based on measurements that form different profiles of different paths. Classifier 521 stores each set 522J of internal values in memory 505 in association with a corresponding label (e.g. the character string value "leftwrist-leftarmpit" of label 523J in FIG. 5) of a pair of locations at which are located the pair of electronic devices 101, 102 used to generate the set 522J of internal values (based on measurements of the AC signal traveling through body 100 between locations identified by label 523J).

Classifier 521 is then used during normal operation, to determine the path 103, which is in turn used to determine functionality and/or operational characteristic(s) of electronic device 102. During calibration, internal values 522 (FIG. 5) are stored in memory 505 of computer 500, and subsequently a prediction is done during normal operation, by matching these stored internal values 522 to corresponding internal values which are newly-derived from incoming new data (i.e. based on a set of measurements received from a newly-placed electronic device 102). Thus, by computations that use the stored internal values of the classifier with new measurements, electronic device 102 is configured for its own normal operation, based on identification of its location on body 100 (e.g. the label "leftarmpit" in FIG. 4D), which in turn is based on classifier's identification of a path 103 (the character string value "leftwrist-leftarmpit" of label 523J in FIG. 5) between electronic devices 101 and 102 (for example, a new profile is determined to be closest to one of multiple profiles used to train the classifier).

Figure 2A:
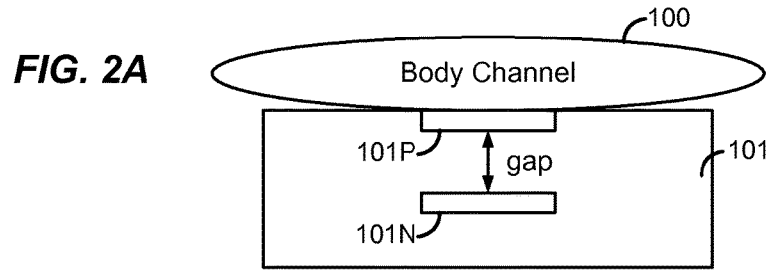
FIG. 2A illustrates a dual electrode system in a vertical orientation that provides capacitive coupling of electrical circuitry (e.g. AC transmitting or AC receiving circuitry or combination) with direct skin contact of body 100 of FIG. 1A.
Figure 2B:
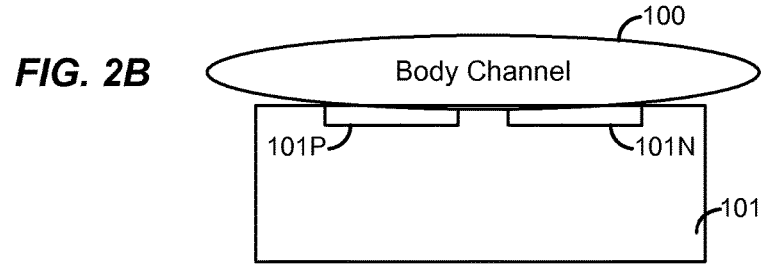
FIG. 2B illustrates a dual electrode system in a horizontal orientation that provides galvanic coupling of electrical circuitry (e.g. AC transmitting or AC receiving circuitry or combination). Galvanic coupling requires that both electrodes of the dual electrode system make direct skin contact with body 100 of FIG. 1A.
Figure 2C:
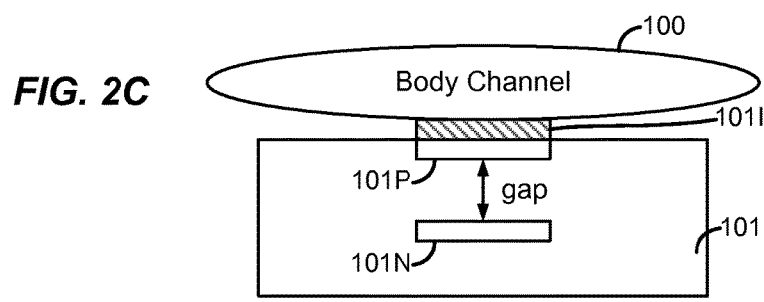
FIG. 2C illustrates a dual electrode system in a vertical orientation wherein electrical circuitry (e.g. AC transmitting or AC receiving circuitry or combination) does not make direct skin contact with body 100 of FIG. 1A.
Figure 2D:
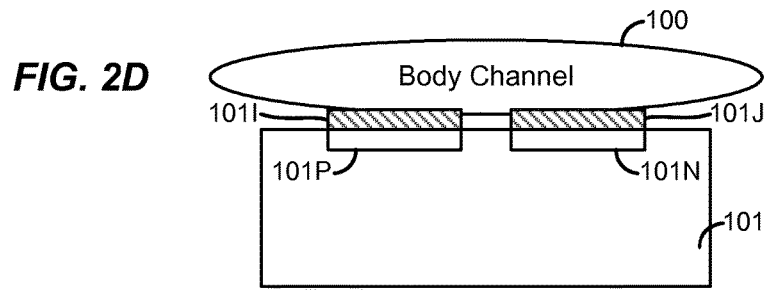
FIG. 2D illustrates a dual electrode system in a horizontal orientation wherein electrical circuitry (e.g. AC transmitting or AC receiving circuitry or combination) does not make direct skin contact with body 100 of FIG. 1A.
Figure 3A:
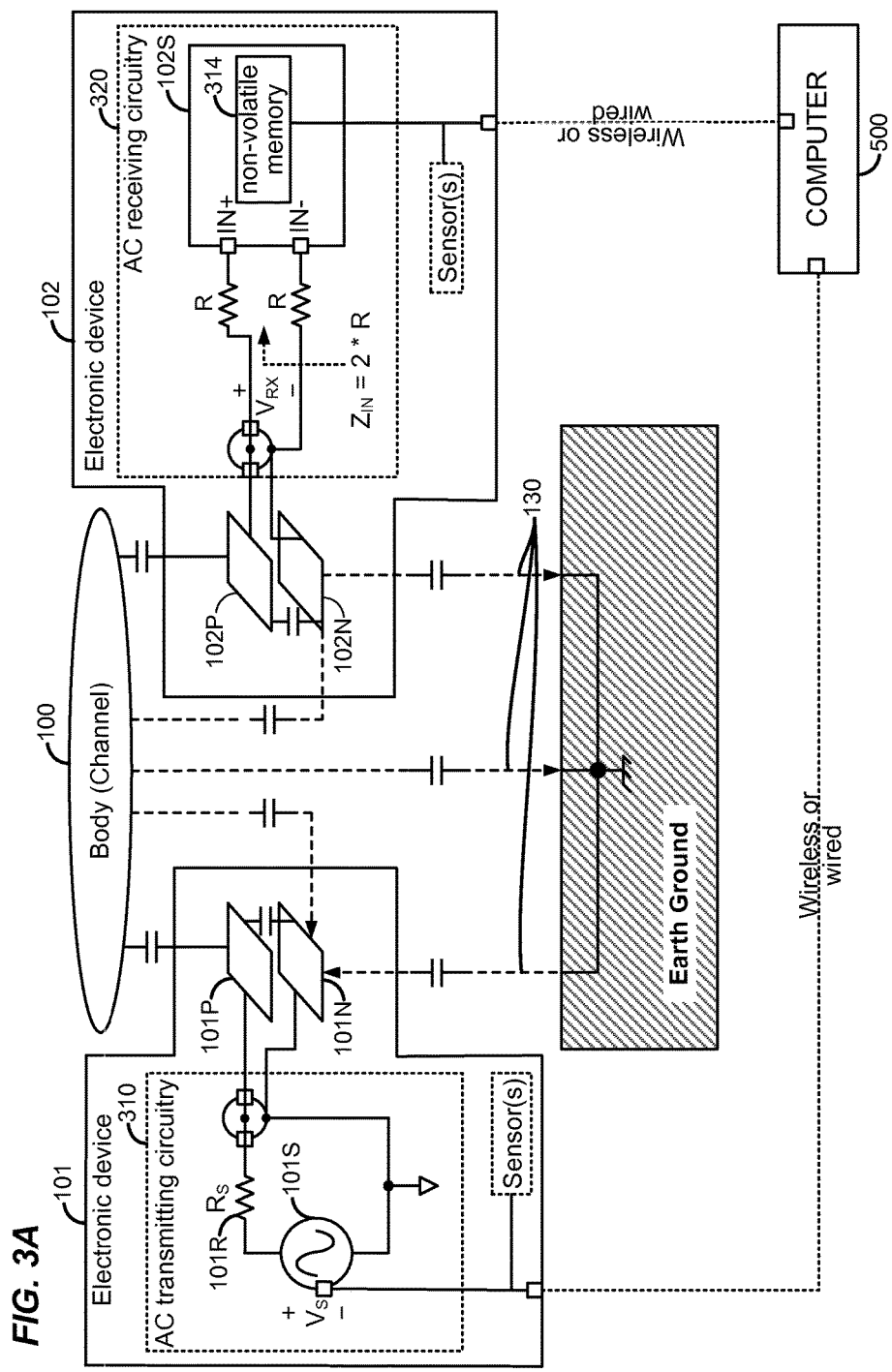
FIG. 3A illustrates, in a high-level circuit diagram, electrical coupling between a pair of electronic devices 101 and 102 and a body channel 100, in some implementations of the type illustrated in FIGS. 1A-1B and 2A-2D.

In order to enable a particular path of an AC signal to pass through body 100, electronic devices 101, 102, 104 and 106 (which may be operable as AC transmitting devices and/or operable as AC receiving devices) contain electrodes that are either present on the surface of the device and in direct contact with skin (as shown in FIGS. 2A and 2B) or the electrodes are inside the device and capacitively coupled to the skin of body 100 (as shown in FIGS. 2C and 2D). Depending on the implementation and location of two electronic devices at two ends of a path, body 100 may form a channel that transmits an AC signal, as illustrated in FIG. 3A when electrodes 101P, 101N and 102P, 102N of the two electronic devices are coupled to body 100. FIGS. 2A, 2B, 2C, and 2D illustrate four different construction type implementations, for coupling of body 100 to electrodes 101P, 101N of AC transmitting circuitry 310 in electronic device 101 in FIG. 3A. These same four different construction type implementations may also be made, for coupling of body 100 to electrodes 102P, 102N of AC receiving circuitry 320 in electronic device 102 in FIG. 3A, or for a combination of AC transmitting and receiving circuitry (e.g. in electronic device 101 in FIG. 3D), as described herein Specifically, FIG. 2A illustrates one construction type of an electronic device 101, wherein body 100's channel is in direct contact with only the positive electrode 101P that in turn is separated by a gap from a negative electrode 101N. FIG. 2B illustrates another construction type wherein body 100's channel is in direct contact with both positive electrode 101P and negative electrode 101N. FIG. 2C illustrates yet another construction type wherein body 100 is capacitively coupled through insulation 101I to only the positive electrode 101P that in turn is separated by a gap from a negative electrode 101N. Finally, FIG. 4D illustrates yet another construction type wherein body 100's channel is capacitively coupled via insulating material 101I and 101J to each of positive electrode 101P and negative electrode 101N. Examples of insulation 101I and 101J may be a housing of electronic device 101.

A manufacturer of such electronic devices decides which construction type and which circuitry is the best, for a given application. More specifically, a manufacturer may decide they do not want a user to be able to see the positive electrode 101P, in which case the positive electrode 101P may be housed inside a housing of electronic device 101, which still permits capacitive coupling to body 100 (despite the fact there is insulating material 101I, 101J in between). However, circuitry implemented in an electronic device 101 of the type shown in FIG. 2C may include different passive and/or active components relative to circuitry implemented inside a device of the type shown in FIG. 2A. More specifically, AC transmitting circuitry within electronic device 101 of FIG. 2C may generate an AC electrical signal of voltage higher in magnitude than voltage generated by corresponding circuitry implemented in an electronic device of the type shown in FIG. 2A. Also, the value $R_S$ of a resistor 101R (see FIG. 3A) may be different for the devices of FIGS. 2A and 2C, because the load characteristic is different.

In some implementations, AC transmitting circuitry 310 within electronic device 101 includes a dual electrode signal generator 101S (FIG. 3A) that generates a single-ended output voltage $V_S$ that varies with time, and thus supplies an alternating current (AC) signal between positive electrode 101P and negative electrode 101N (FIG. 3A). In an alternative implementation, electronic device 101 which is operable as an AC transmitting device may include a dual electrode signal generator that generates a differential output voltage across the positive electrode 101P and negative electrode 101N. Positive electrode 101P is coupled to dual electrode signal generator 101S via a resistor 101R of value $R_S$ that is implementation specific, and determined by matching the impedance present by the load that is formed by a dual electrode system consisting of positive electrode 101P and negative electrode 101N being electrically coupled to body 100. In FIG. 3A, negative electrode 101N is connected to local ground in electronic device 101, which is at the same potential as the negative terminal of dual electrode signal generator 101S.

In several implementations, positive electrode 101P of electronic device 101 is in direct contact with skin of body 100. Hence, an AC signal that is output at the electrodes of electronic device 101 which is operable as an AC transmitting device flows through skin, tissue and organs of body 100 to electronic device 102 (FIG. 3A) which is operable as an AC receiving device. In some implementations, AC receiving circuitry 320 within electronic device 102 includes a dual electrode sensor 102S that receives differential input from body 100 between positive electrode 102P and negative electrode 102N (FIG. 3A). Positive electrode 102P and negative electrode 102N are coupled via respective resistors of resistance R to the input terminals of dual electrode sensor 102S. Dual electrode sensor 102S measures voltage and/or phase angle of the AC signal received from body 100 and stores measurements in a non-volatile memory therein (e.g. non-volatile memory 314, described below in reference to FIG. 3C) A return path 130 for the AC signal is through the environment.

Each of electronic devices 101 and 102 may be coupled to a computer 500 in which is implemented a classifier, e.g. based on a neural network. Depending on the implementation, computer 500 may be included in a third device, such as a hand-held electronic device, e.g. a smartphone, or a tablet. In some implementations, computer 500 is physically housed in electronic device 101 that includes AC transmitting circuitry 310 (and which is operated as a hub in some implementations).

Figure 3B:
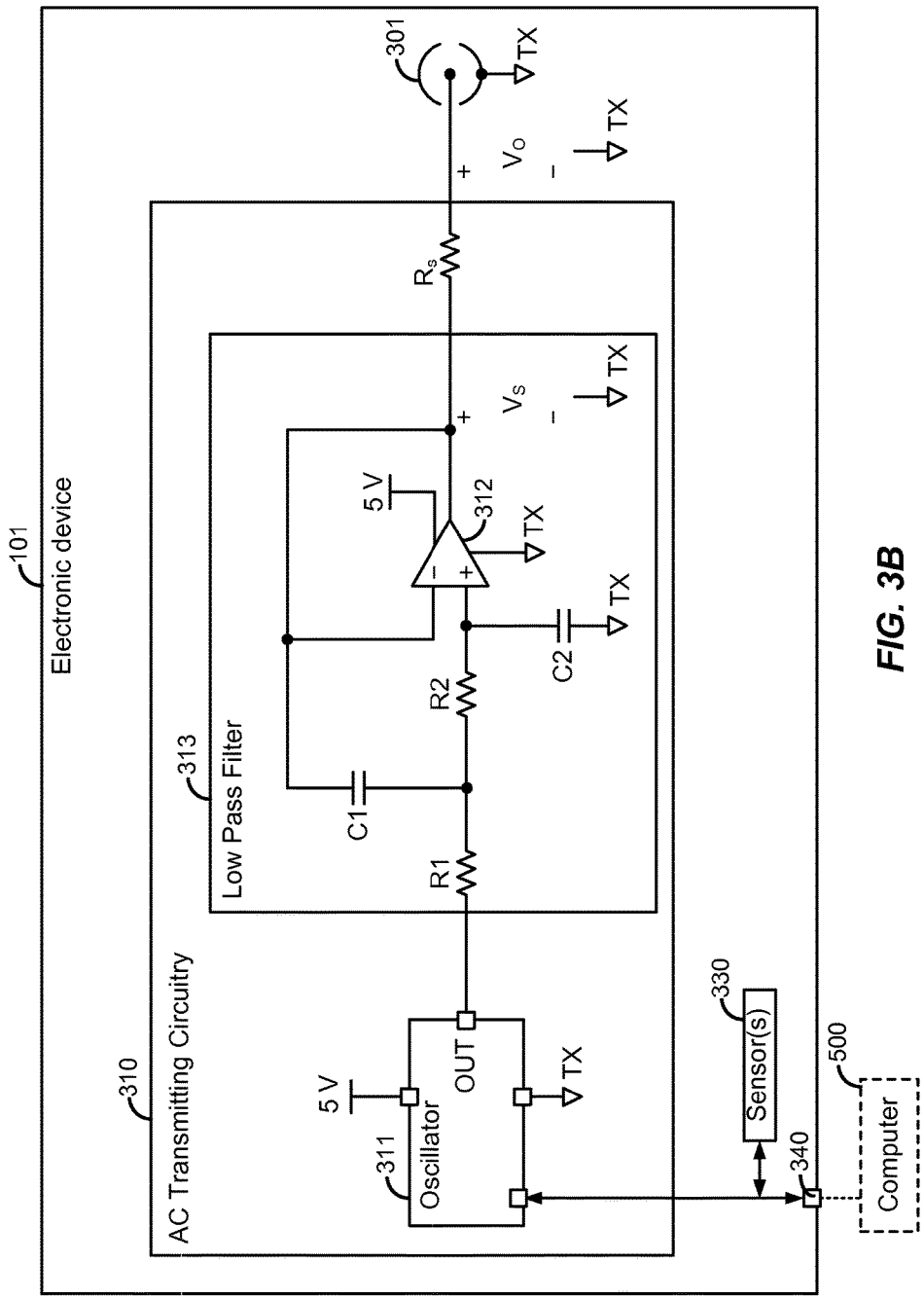
FIG. 3B illustrates, in an intermediate-level circuit diagram, AC transmitting circuitry in electronic device 101 that is configured to transmit an AC electrical signal through the body 100 of FIG. 3A.

AC transmitting circuitry 310 may be implemented as illustrated in FIG. 3B, including an oscillator 311 configured to generate a square wave signal at either multiple discrete frequencies which are predetermined (e.g. based on input from computer 500), or possibly a continuous sweep across a frequency range. Oscillator 311 may have an input coupled directly or via a transceiver 340 to computer 500, to receive therefrom the just-described discrete frequencies and/or the frequency range. Coupled to the output of oscillator 311 (in AC transmitting circuitry 310 of FIG. 3B) is a low pass filter 313 in electronic device 101 that converts the square wave signal from oscillator 311 into a sine wave that is supplied as the output voltage $V_S$. The low pass filter 313 in electronic device 101 of some implementations includes an operational amplifier 312. In addition to operational amplifier 312, the low pass filter 313 includes (as shown in FIG. 3B) several passive components (e.g. resistors R1 and R2 and capacitors C1 and C2), readily apparent to the skilled artisan in view of this detailed description. The output of low pass filter 313 is coupled via a resistor of value $R_S$ to a connector 301 of a dual electrode system. As noted above, the dual electrode system consists of a positive electrode and a negative electrode of connector 301 electrically coupled to body 100.

Figure 3C:
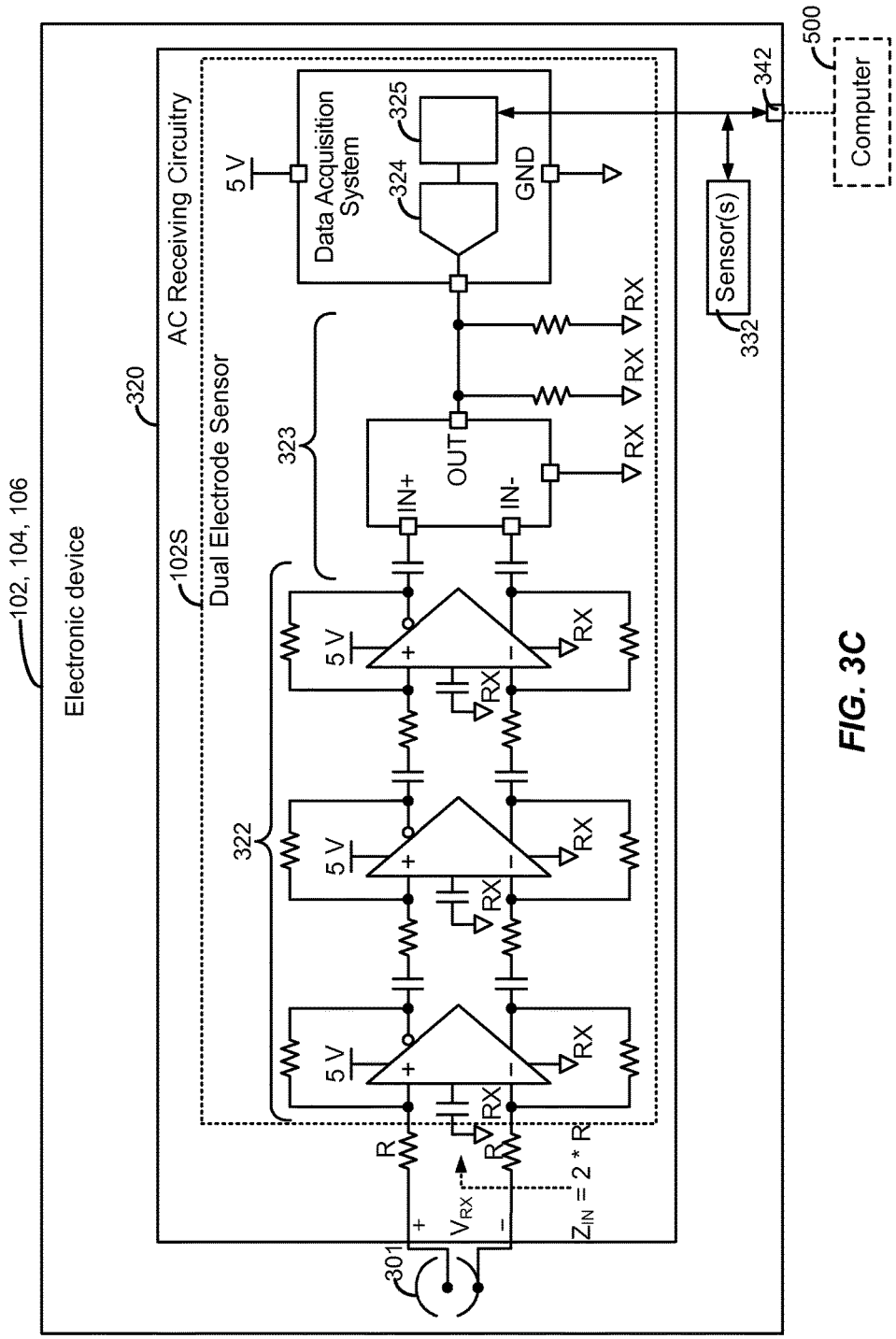
FIG. 3C illustrates, in an intermediate-level circuit diagram, AC receiving circuitry in electronic device 102 that is configured to receive and measure the AC electrical signal through the body 100 of FIG. 3A.

In some implementations, in AC receiving circuitry 320 of electronic device 102 (see FIG. 3C), a dual electrode sensor 102S includes a three-stage fully differential amplifier system 322. In addition to the three-stage fully differential amplifier system 322, the dual electrode sensor 102S includes (as shown in FIG. 3C) a RF log detector 323 that is coupled in series with the three-stage fully differential amplifier system 322. RF log detector 323 provides a log-linear coefficient between a radio frequency (RF) input voltage and its output. More specifically, RF log detector 323 includes a series of detector cells that rectify the input signal and produce an output current which is log-linearly related to input power.

The output of RF log detector 323 is connected within dual electrode sensor 102S to an analog-to-digital converter 324 that stores digital values (e.g. 10 bits in length) in non-volatile memory 325, which is coupled via a transceiver 342 to a computer 500. Transceiver 342 may be coupled to computer 500 wirelessly or by wire(s), depending on the implementation. In some implementations, computer 500 may be programmed to interoperate with electronic device 102, e.g. to trigger multiple measurements by analog-to-digital converter 324 at multiple frequencies, to obtain a set of measurements (that form a profile of a path) which are stored in non-volatile memory 325 and transferred to computer 500. Analog-to-digital converter 324 and non-volatile memory 325 may be implemented in electronic device 102 in the form of a data acquisition system.

Figure 3D:
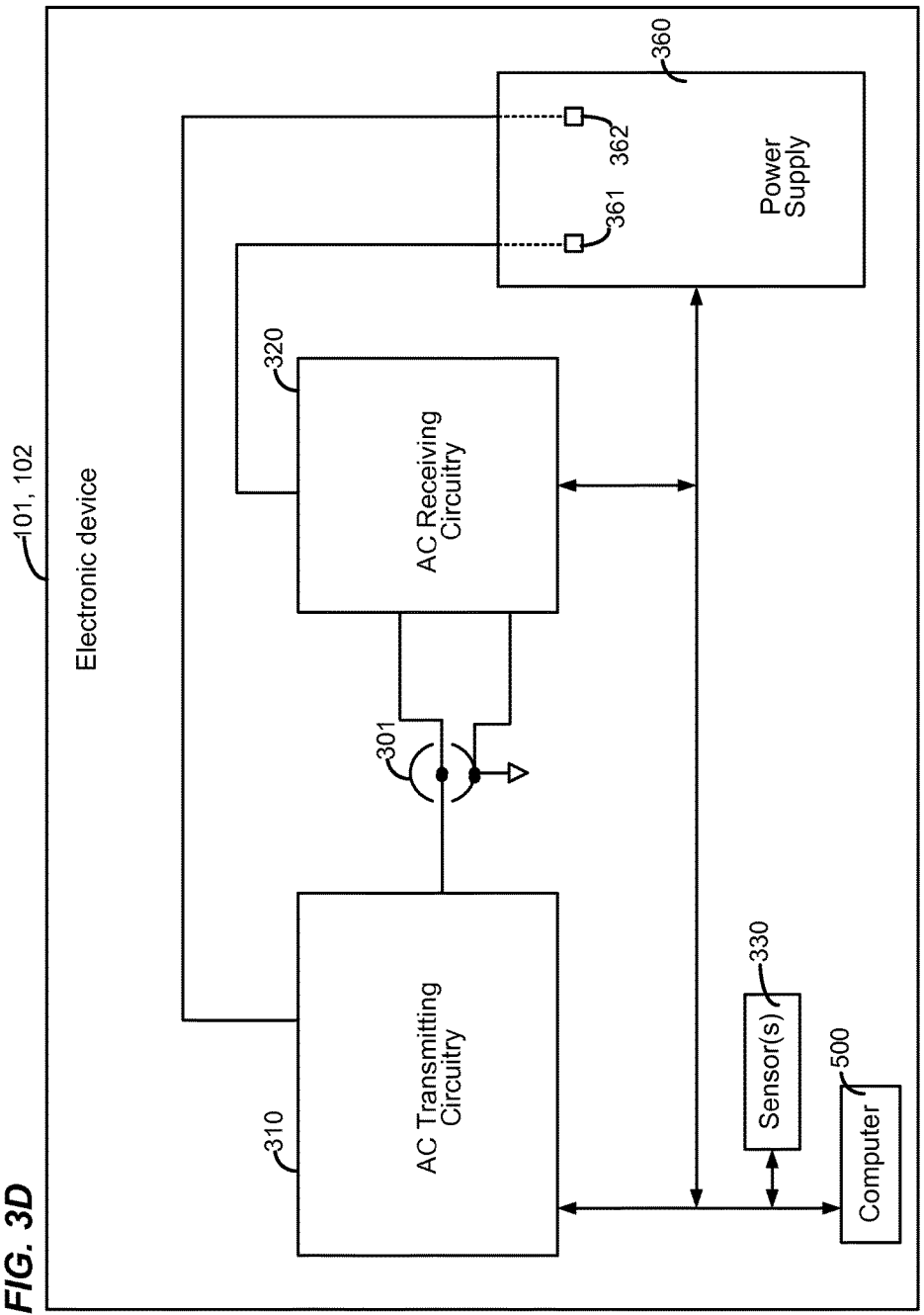
FIG. 3D illustrates, in a block-level diagram, electronic device 101 that includes a combination of AC transmitting circuitry 310 and AC receiving circuitry 320, and which is configurable as an AC transmitting device or an AC receiving device, in some exemplary implementations.

In addition to AC transmitting circuitry 310 (FIG. 3B), some implementations of electronic device 101 may additionally include AC receiving circuitry 320 (FIG. 3C) both of which may be coupled to the same dual body system connector 301, as illustrated in FIG. 3D. Electronic device 101 of the type shown in FIG. 3D may additionally include one or more sensor(s) 330. Electronic device 101 of FIG. 3D may be configured as a transmitter, e.g. by disabling power supplied to AC receiving circuitry 320 or alternatively configured as a receiver, e.g. by disabling power supplied to AC transmitting circuitry 310. Specifically, a power supply 360 (FIG. 3D) receives input from computer 500 (e.g. via transceiver 340) and operates one of switches 361 or 362 (e.g. power FET) to turn on and/or turn off power to AC receiving circuitry 320 or to AC transmitting circuitry 310 respectively, thereby to enable and/or disable these respective circuitries. Thus, FIG. 3D illustrates a generic electronic device, which may implement electronic device 101 for use as a transmitter of an AC signal or electronic device 102 for use as a receiver of the AC signal, wearable at any location on body 100.

In some implementations, the generic electronic device (FIG. 3D) includes a computer 500 that is coupled to power supply 360 to operate the switches 361 and 362 to set up electronic device 101 as a transmitter or electronic device 102 as a receiver of the AC signal that passes through body 100, during a training phase and/or during normal operation. Moreover, computer 500 may implement a classifier that selects a location on body 100 (from among predetermined locations identified in the training phase), to configure sensor(s) 330 in electronic device 101 or electronic device 102 for normal operation. In some implementations, computer 500 is not included in either of electronic device 101 or electronic device 102 and instead computer 500 is included in another device, such as a smartphone, tablet, laptop, or desktop PC. In the just-described implementations, the generic electronic device may include a transceiver 340 shown in electronic device 101 of FIG. 3B. Transceiver 340 may be coupled to computer 500 wirelessly or by wire(s), depending on the implementation.

Figure 3E:
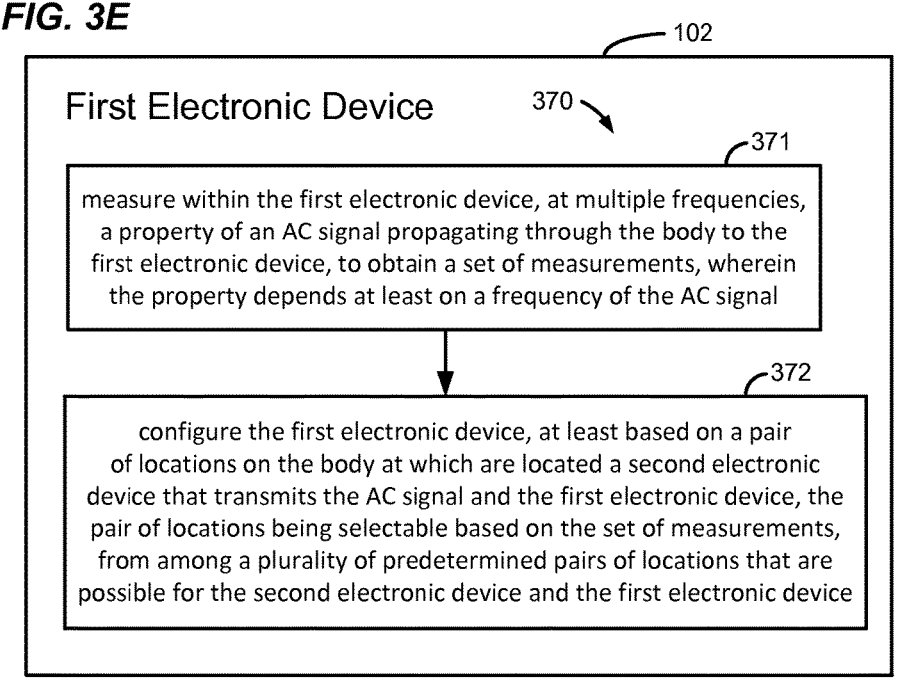
FIG. 3E illustrates, in a high-level flow chart, acts 371 and 372 performed by electronic device 102 (also called "first electronic device"), in many implementations.

Many implementations implement a method 370 that includes performance of acts 371 and 372 illustrated in FIG. 3E by an electronic device. Specifically, the method 370 includes in act 371, measuring within a first electronic device (e.g. electronic device 102), at multiple frequencies, a property of an AC signal propagating through body 100 to the first electronic device (e.g. electronic device 102), to obtain a set of measurements. In the just-described implementations, the property being measured depends at least on a frequency of the AC signal. In several such implementations, the property being measured in the first electronic device is indicative of a loss of the AC signal, at least due to propagation through body 100 from the second electronic device (e.g. electronic device 101). After act 371, the method 370 includes performing an act 372, by configuring the first electronic device (e.g. electronic device 102), at least based on a predetermined pair of locations on body 100 at which are located the first electronic device (e.g. electronic device 102) and a second electronic device that transmits the AC signal (e.g. electronic device 101). The just-described predetermined pair of locations may be selectable based on the set of measurements, from among a plurality of predetermined pairs of locations that are possible for the second electronic device (e.g. electronic device 101) and the first electronic device (e.g. electronic device 102).

In several implementations of the type described in the immediately-preceding paragraph above, the first electronic device which performs acts 371 and 372 of FIG. 3E interoperates with the second electronic device which may be configured to perform a method 380 that includes acts 381 and 382 of FIG. 3F as follows. Specifically, the method 380 includes in act 381, generating an AC signal at multiple frequencies in the second electronic device (e.g. electronic device 101), and then transmitting the AC signal through body 100. After act 381, the method 380 includes performing an act 382, by the second electronic device (e.g. electronic device 101) receiving a set of measurements from the first electronic device (e.g. electronic device 102), and using a previously-trained classifier to select a predetermined pair of locations at which are located the second electronic device and the first electronic device. As noted above in the immediately-preceding paragraph, the predetermined pair of locations are selected based on the set of measurements, from among a plurality of predetermined pairs of locations, on which the classifier has been trained. Accordingly, in implementations of the type illustrated in FIG. 3E, the first electronic device (e.g. electronic device 102) may be configured to enable only AC receiving circuitry (e.g. by turning power off to AC transmitting circuitry 310 and/or computer 500 if present therein as illustrated in FIG. 3D).

Figure 3F:
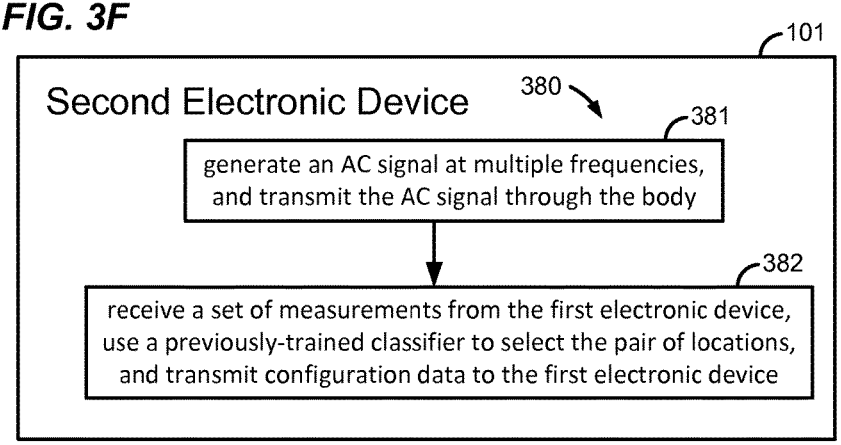
FIG. 3F illustrates, in a high-level flow chart, acts 381 and 382 performed by an electronic device 101, (also called "second electronic device") to interoperate with electronic device 102 of FIG. 3E, in some implementations.

In some implementations of the type described in the preceding two paragraphs above in reference to FIGS. 3E and 3F, the previously-trained classifier may be any classifier, e.g. a neural network that is trained on a plurality of sets of measurements of the property (e.g. a plurality of profiles) corresponding to the plurality of predetermined pairs of locations. In the plurality of sets of measurements, each set of measurements (i.e. each profile, which includes measurements at different frequencies, e.g. of the amplitude of the scattering parameter $S_{21}$) corresponds to one pair of locations (e.g. leftwrist-chest). In several such implementations, the plurality of pairs of locations comprises a group of pairs of locations (e.g. leftwrist-leftarmpit, leftwrist-lefthandmiddlefinger, leftwrist-chest and leftwrist-rightwrist), such that one location in each pair of locations in the group is a common known location (e.g. leftwrist), at which the second electronic device (e.g. electronic device 101) is located on the body, as a transmitter of the AC signal. In these just-described implementations, identification of a pair of locations (e.g. by the label leftwrist-chest) in computer 500 automatically identifies a receiving location within the pair, based on the common known location included in the pair being known to computer 500 (e.g. identified by the label leftwrist). In several such implementations, computer 500 performs a single training phase to use only one common known location (e.g. identified by the label leftwrist), and thereafter identifies each predetermined pair of locations with only the label of a receiving location contained in each predetermined pair, by omitting the label (e.g. leftwrist) of the common known location.

In several implementations, two or more electronic device(s) of the type illustrated in FIGS. 3A-3F are worn on body 100 during a training phase of computer 500 which includes two operations, namely a setup operation 410 (FIG. 4A) wherein a single electronic device is set up as a transmitter (e.g. electronic device 101 worn on left wrist as shown in FIG. 1A) and other such electronic devices are set up as receivers (e.g. electronic devices 102, 104, 106 and 111) and initialized correspondingly in computer 500.

The setup operation 410 is followed by a calibration operation 420 (FIG. 4A) in which measurements are made of AC signals traveling along a group of predetermined paths A . . . J . . . N through body 100, between corresponding predetermined pairs of locations on body 100, e.g. as illustrated in FIG. 1A from electronic device 101 (operable as a common AC transmitting device) to one or more electronic device(s) 102, 104, 106, 111 (operable as AC receiving devices), and measurements of the AC signals are transmitted to computer 500. Computer 500 receives these measurements and uses them to train a classifier 521 therein. As noted above, in the just-described paths, a common known location (e.g. left wrist) of the electronic device 101 (which is operable as the common AC transmitting device) forms a starting point (also referred to as a common predetermined location) that is common to all paths 103, 105, 107 and 121. Accordingly, classifier 521 is implemented in some implementations by processor 506 executing software, which may be in the form of one or more sequence(s) of instructions stored in memory 505. Classifier 521 is trained during one or more training phase(s) to identify one or more pair(s) of locations of two or more electronic devices on body 100, based on measurements of one or more attributes of a scattering parameter, e.g. amplitude or phase angle or both, as illustrated in FIG. 1B or FIG. 1C or both, depending on the implementation.

After calibration operation 420 (FIG. 4A), one or more of electronic devices 101, 102, 104, 106 and 111 may be removed from body 100. Subsequently, when an electronic device is attached to body 100, in certain implementations (e.g. single-training-phase implementations), the two or more electronic devices enter a normal operation phase, which includes two operations performed by computer 500, namely a path-determination operation 430 (FIG. 4A), followed by a configuration operation 440.

In path-determination operation 430 (FIG. 4A), a newly-attached electronic device is set up as a receiver, and an AC receiving circuit in the newly-attached electronic device measures at least one scattering parameter of the AC signal at multiple frequencies, and a set of these measurements (which form a profile) are transmitted to computer 500. Computer 500 receives the set of measurements from the newly-attached electronic device and operates classifier 521, which classifies the newly-received set of measurements to select a particular path J from among the group of predetermined paths A . . . J . . . N that have been calibrated in calibration operation 420.

In the configuration operation 440 (FIG. 4A), the newly-attached electronic device is determined to be located at the ending point of the particular path J, and is then configured by computer 500 to perform a specific functionality (e.g. collect certain data) and/or operate with a specific characteristic (e.g. at a certain data rate). Computer 500 may be included in electronic device 101 and/or included in one or more of electronic device(s) 102, 104, 106, 111 that may be operable in any combination as AC transmitting and receiving devices, or computer 500 may be implemented in still another device, such as a mobile phone and connected by a wired or wireless network to one or more of electronic device(s) 101, 102, 104, 106, and/or 111.

In some implementations (e.g. multiple-training-phase implementations), calibration operation 420 (FIG. 4A) is followed by an act 427 to check if another phase of training is necessary, and if the answer is yes, then control returns to setup operation 410 via branch 428 (FIG. 4A) wherein another electronic device is set up as a transmitter, or a transmitter used in a previous iteration of setup operation 410 and calibration operation 420 is moved to a new location. Thereafter, calibration operation 420 is performed as described above, followed by act 427 again, to check if yet another phase of training is needed. In some such implementations, multiple phases of training are needed and hence corresponding iterations are performed via branch 428, and thereafter when the answer in act 427 is no, control transfers to normal operation, e.g. perform path-determination operation 430 as briefly described above, and in detail below.

In certain multiple-training-phase implementations, a number of phases of training depends on how many electronic devices are placed on a body. In several such implementations, a number Y of predetermined pairs of locations that can be characterized, based on a number X of electronic devices placed on the body is expressed as $Y=0.5X(X-1)$. For example, when X=4 electronic devices are simultaneously worn on a body, up to $Y=0.5*4*(4-1)=6$ predetermined pairs of locations may be characterized, wherein 3 predetermined pairs of locations are characterized in a first training phase, 2 predetermined pairs of locations are characterized in a second training phase, and 1 predetermined pair of locations is characterized in a third training phase Setup operation 410 (FIG. 4A) of some implementations includes acts 411-416 illustrated in FIG. 4B. Specifically, in act 411, an AC electrical signal is sent by an electronic device (e.g. electronic device 101) through body 100. When the electronic device that performs act 411 is the only electronic device (and hence the first device) which is attached to body 100, such as electronic device 101 (which may include a combination of AC transmitting circuitry and AC receiving circuitry), in an act 412 (FIG. 4B) electronic device 101 listens for a return signal for a certain duration, which may result in a time out, based on which electronic device 101 determines that it is the only device on body 100 and therefore electronic device 101 goes to act 413. In act 413 (FIG. 4B), electronic device 101 defines itself to be a transmitter (also called "hub") and notifies computer 500. Computer 500 stores in a memory, an identity and a location of electronic device 101 as the common predetermined location. The location of electronic device 101 (FIG. 1D) may be identified via user input, e.g. as a string of characters "leftwrist" which may be input directly to computer 500, or via electronic device 101 depending on the implementation. In act 414 (FIG. 4B), electronic device 101 checks to see if there are other devices that are to be configured. Initially, when electronic device 101 is the only device (and hence the first device) attached to body 100, then the answer is no and electronic device 101 proceeds to act 416 to check if there is at least one receiver, and if not returns to act 411 (described above). When act 414 is performed, if two electronic devices are already attached to body 100, the answer is yes in act 414 (because there are additional devices to be configured), so control returns to act 411.

When an additional electronic device is attached to body 100 at any time, such as electronic device 102 (which may contain only AC receiving circuitry in some implementations), then whenever act 412 (FIG. 4B) is performed, a return signal transmitted by electronic device 102 is detected by electronic device 101. The return signal may be received by electronic device 101 wirelessly over the air, in implementations of electronic devices 101 and 102 that contain wireless circuitry. Depending on the implementation, the return signal may be wirelessly transmitted by electronic device 102 in conformance with any industry standard, e.g. WiFi, or Bluetooth. Also depending on the implementation, a return signal that is transmitted wirelessly may be modulated in any manner, e.g. pulse-width modulation, frequency modulation, amplitude modulation, or any combination thereof. Alternatively, the return signal may be received through body 100 using intrabody signal propagation in implementations wherein electronic device 101 contains AC receiving circuitry and electronic device 102 contains AC transmitting circuitry.

When there are at least two such devices attached to body 100, the no branch is taken from act 412 (FIG. 4B) to act 415. In act 415, a handshake procedure is performed between electronic devices 101 and 102, resulting in electronic device 102 being configured as a receiver of an AC electrical signal. At this stage, the identity of electronic device 102 is notified to computer 500, which stores the identity in memory 505. On completion of the handshake, control returns to act 414. At this stage, when the only electronic devices on body 100 are electronic devices 101 and 102, the answer in act 414 is no, and act 416 is performed in which the answer is yes, there is at least one receiver (namely electronic device 102), and hence calibration operation 420 is performed subsequently, as follows.

Figure 4C:
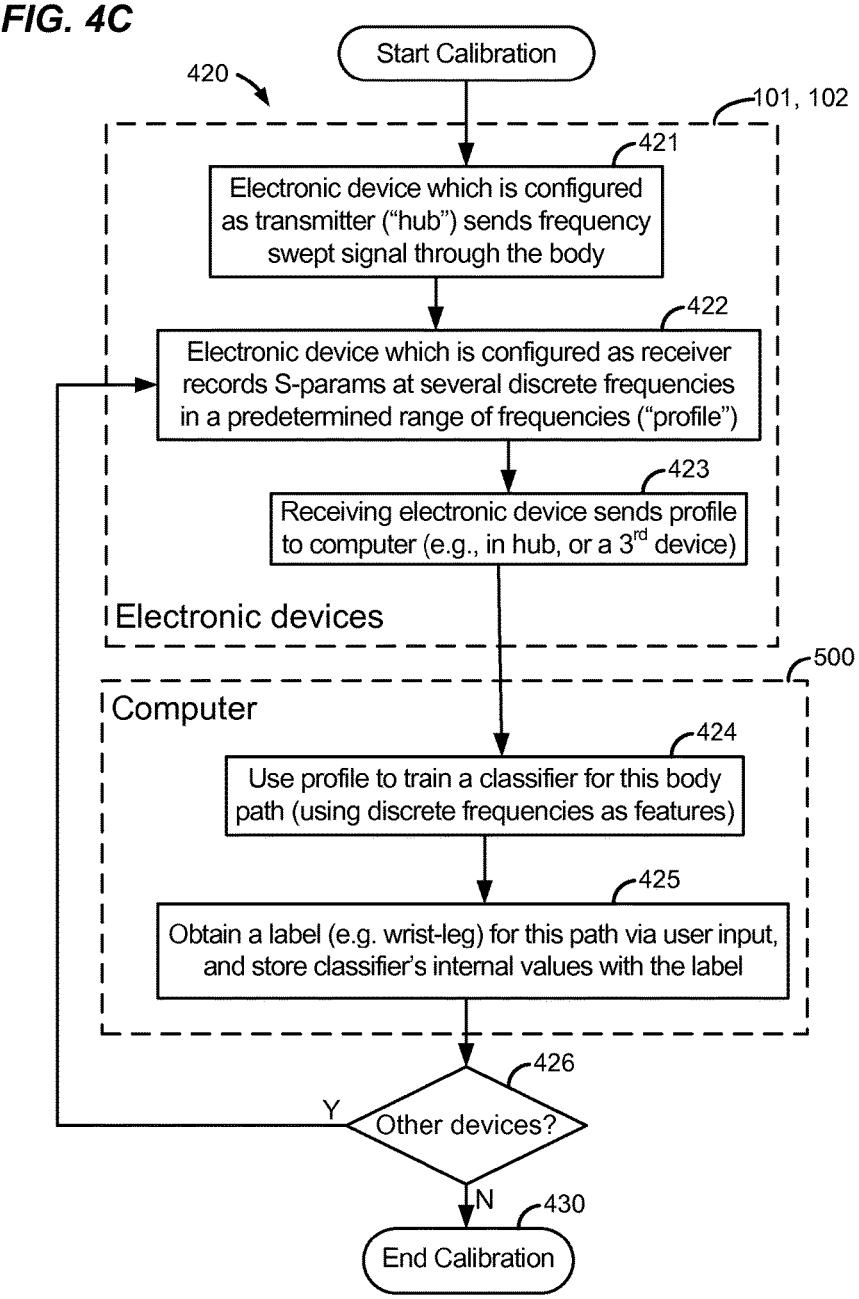
FIG. 4C illustrates, in another flow chart, acts performed by computer 500 in some implementations, in a calibration operation 420 in FIG. 4B.

Calibration operation 420 (FIG. 4A) of some implementations includes acts 421-426 illustrated in FIG. 4C. Specifically, in act 421, a frequency-swept AC signal is sent through the body 100 by an electronic device which is configured as an AC transmitter (or hub), e.g. electronic device 101. Subsequently, in act 422 (FIG. 4C), a receiver, such as electronic device 102 makes a set of measurements (also called profile) of a parameter of the AC electrical signal at multiple frequencies (i.e. several discrete frequencies), such as one or more S-parameters (described above). Then, in act 423 (FIG. 4C), the receiver, e.g. electronic device 102 wirelessly transmits a set of multiple measurements and its location (also called "other predetermined location"), to a computer 500. Electronic device 102 (FIG. 1D) may obtain its location on body 100 via user input therein (e.g. label "leftarmpit"), or alternatively such user input may be received directly in computer 500. Computer 500 may be included in, for example, electronic device 101 (the transmitter or hub) in which case the multiple measurements (or profile) may be included in a return signal, or computer 500 may be included in another electronic device, such as a hand-held device (e.g. smartphone).

Thereafter, in an act 424 (FIG. 4C), the measurements are used by computer 500 to train a classifier 521 which generates internal values that are then stored by computer 500 in non-volatile memory in act 425, and labeled with a string of characters that identify the path between the two electronic devices 101 and 102. For example, in multiple-training-phase implementations, a path's label "leftwrist-leftarmpit" may be obtained by computer 500 automatically concatenating the two character strings obtained via user input: a first character string identifying a common predetermined location of electronic device 101 e.g. label "leftwrist", and a second character string identifying another predetermined location of electronic device 102, e.g. label "chest". For example, in single-training-phase implementations, a path's label "leftarmpit" may be obtained by computer 500 using just the character string identifying the receiving location of electronic device 102 in the path, e.g. label "leftarmpit" because the common predetermined location of electronic device 101 e.g. label "leftwrist" is known and does not change.

After act 425, in an act 426 (FIG. 4C), a check is made (e.g. by computer 500 in electronic device 101) as to whether there are other electronic devices attached to body 100. If the answer in act 426 is yes, control returns to act 422 (described above), followed by performance of acts 422-426 with another electronic device which is also configured as a receiver, at a different other predetermined location, e.g. electronic device 104 or 106 (FIG. 1A), whereby an additional profile is generated for a corresponding path (e.g. path 105 or 107) from the common predetermined location, and the additional profile is used to additionally train classifier 521. When no more electronic devices are found in act 426, the trained classifier 521 (with its internal values 522 and corresponding path labels 523 stored in non-volatile memory 505, as shown in FIG. 5) is used by computer 500 in normal operation, to identify a particular path (e.g. path 103 in FIG. 1A) between a transmitter (e.g. electronic device 101) and a receiver (e.g. electronic device 102), in a path-determination operation 430, as follows.

Path-determination operation 430 (FIG. 4A) of some implementations includes acts 431-437 illustrated in FIG. 4D. Specifically, in act 431, an electronic device 101 is attached to the common predetermined location, and an electronic device 102 is newly attached to any other predetermined location which was previously used in calibration operation 420 (e.g. to train classifier 521). Subsequently, in act 432 (FIG. 4D), electronic device 101 acting as a transmitter, sends the frequency-swept AC signal through body 100. Thereafter, in act 433 (FIG. 4D), the electronic device 102 acting as a sensor makes a set of multiple measurements (at multiple frequencies), followed by act 434 in which the set of measurements are sent to computer 500, to one or more processor(s) 506 therein. Then, in an act 435 (FIG. 4D), the classifier 521 is operated by computer 500 on the set of measurements (or profile), to identify from among paths A . . . J . . . N, a particular path J through body 100 at the end of which is located the newly-attached electronic device 102.

In some implementations, determination of a particular path J (e.g. labeled leftwrist-leftarmpit) through body 100 is used to identify (in act 435) a specific other predetermined location on body 100 at which the electronic device 102 is newly attached (e.g. leftarmpit). For example, in multiple-training-phase implementations, computer 500 deletes from a label of a path that contains two character strings, the label of the common predetermined location (e.g. leftwrist) at which the electronic device 101 is operable as an AC transmitting device, thereby to obtain a label of the specific other predetermined location, at which the electronic device 102 is newly attached (e.g. leftarmpit). In single-training-phase implementations wherein each path contains only one location's label, computer 500 identifies a label of a path (e.g. leftarmpit), as the label of the specific other predetermined location, at which the electronic device 102 is newly attached.

Identification of the specific other predetermined location of an electronic device 102 enables electronic device 102 to be automatically configured for optimal performance (e.g. for its location, at the left ankle). Thus, depending on the implementation, computer 500 or electronic device 101 (operating as a "hub"), use the particular location of electronic device 102 (identified by use of classifier 521 in act 435) to look up associations (FIG. 4D) in a non-transitory storage media 438, between locations identified by labels 441 and corresponding configurations 439, to obtain a specific configuration, e.g. configuration J for the particular location "leftarmpit." The configuration J is transmitted to the newly-attached electronic device, e.g. electronic device 102. The configuration J may be transmitted by computer 500 (or by electronic device 101) with a key to the newly-attached electronic device. Thereafter, a check is made in act 437 (e.g. by computer 500) as to whether there are any other electronic devices attached to body 100, and if yes then control returns to act 433 (described above), and if no then a configuration operation 440 is performed.

In operation 440, the newly-attached electronic device (e.g. electronic device 102) uses a key (when received) in decoding configuration J (when decoded). Thereafter, in operation 440, configuration J is used to automatically configure the newly-attached electronic device for its normal operation (e.g. by powering off a sensor 332 (FIG. 3C) which contains pulse monitoring circuitry, when the location of electronic device 102 is identified by the label "leftarmpit"). A specific change in operation done by electronic device 102 which receives configuration J (identified based on a set of measurements of the AC signal sent therefrom) depends on implementation, for example as follows.

In certain implementations ("first implementations") of configuration operation 440, an electronic device 102 containing an activity sensor when worn on a leg is automatically configured to use larger thresholds in determining that a step was taken by body 100, relative to automatic configuration of a similar device worn on the wrist or the waist (which may trigger on lower thresholds). Other implementations ("second implementations") of configuration operation 440 optimize battery power usage in electronic device 102 based on its predetermined location on body 100, by automatically turning on/off one or more sensor(s) that are known ahead of time to be not needed at that predetermined location. In some implementations, electronic device 102 may be a generic wearable electronic device which contains multiple sensors (e.g. accelerometer, temperature sensor, photoplethysmography (PPG) sensor etc) and includes AC receiving circuitry of the type shown in FIG. 3C. Depending on the implementation, a single electronic device (e.g. electronic device 101) may include a combination of AC transmitting circuitry and AC receiving circuitry as illustrated in FIG. 3D.

In one example of second implementations, when a user is walking, a first signal indicative of motion from a first electronic device (operable at least as an AC receiving device) on the leg might be better quality than a second signal from a second electronic device (also operable at least as an AC receiving device) on the chest, and thus the data transmission for motion could be turned off in the second electronic device on the chest, saving power. In another example of the second implementations, a signal from the second electronic device on the chest might be better quality than a third signal from the first AC receiving device on the leg, and thus the data transmission for pulse could be turned off in the first electronic device on the leg, saving power.

Still other implementations ("third implementations") of configuration operation 440 set data transmission rates of identical copies of an electronic device (operable at least as an AC receiving device) differently relative to one another, e.g. a first electronic device located on a leg of body 100 and containing a sensor for activity monitoring (e.g. accelerometer) may be configured to transmit sensor data at lower rates than a second electronic device on the chest which may be configured to transmit sensor data at higher rates which may be necessary for heart rate (or pulse rate) monitoring.

The above-described configuration operation 440, which is based on a receiving device's location on body 100, also enables a single receiving device to be automatically re-configured in several illustrative implementations, when moved from one other predetermined location on body 100 to any other predetermined location on body 100. Specifically, a user may attach an electronic device 101 (which is operable as an AC transmitting device) to a first body location (e.g. wrist) which forms a common predetermined location, and the user may attach another electronic device 102 (which is operable as an AC receiving device) to a second body location (e.g. left leg) which forms another predetermined location (by training a classifier), and the user may then use a functionality of the electronic device 102 that depends on the second body location (e.g. counting the number of steps of body 100). Subsequently the same user may move the electronic device 102 to a third body location (e.g. chest) which forms a different other predetermined location (by training the classifier), and the user may then use another functionality of the electronic device 102 which is specific to the third body location, e.g. heart rate monitoring. Thus, several implementations support automatic re-configuration of an electronic device 102, after a change in location on body 100 from one other predetermined location (e.g. chest) to a different other predetermined location (e.g. left leg).

In some implementations, computer 500 is configured to periodically (e.g. once a week) obtain the profiles of paths between electronic device 101 (which is operable as an AC transmitting device) and the electronic device(s) 102, 104, 106, and re-classify these profiles to automatically determine whether there are any changes during the period (e.g. the week), without requiring user intervention. When one of the electronic devices (which is operable at least as an AC receiving device) is attached to body 100 at a new location thereof, a new path causes a new profile to be generated during normal operation of computer 500 (e.g. in path-determination operation 430 shown in FIG. 4D). More specifically, in act 435, classifier 521 in computer 500 attempts to classify this new profile into one of the known profiles (e.g., corresponding to one of the known locations, e.g. chest, leftarmpit, rightwrist). When the new path remains unclassified on completion of act 435, computer 500 is configured to perform calibration operation 420 (see FIG. 4C), wherein the new measurements are used to train the classifier on the new path, resulting in new internal values of a classifier being generated and stored in memory 505 with a new path identifier (e.g. obtained via user input), for use in recognizing the new path when act 435 is performed in future.

Depending on the aspect of the described implementations, a computer 500 that performs one or more of operations 410-440 illustrated in FIG. 4A may be coupled to or included in either an electronic device 101 operable as an AC transmitting device illustrated in FIG. 3B or in an electronic device 102 operable as an AC receiving device as illustrated in FIG. 3C, or in a third device (not shown) that may communicate over a network, wired or wirelessly with either or both of electronic device 101 and/or electronic device 102. The third device may be any mobile station (MS), of the type described herein. As used herein, a mobile station (MS) refers to a device such as a cellular or other wireless communication device (e.g. cell phone), personal communication system (PCS) device, personal navigation device (PND), Personal Information Manager (PIM), Personal Digital Assistant (PDA), laptop or other suitable mobile device which is capable of receiving wireless communications. The term "mobile station" is also intended to include devices which communicate with a personal navigation device (PND), such as by short-range wireless, infrared, wireline connection, or other connection—regardless of whether satellite signal reception, assistance data reception, and/or position-related processing occurs at the device or at the PND.

Also, "mobile station" is intended to include all devices, including wireless communication devices, computers, laptops, etc. which are capable of communication with a server, such as via the Internet, WiFi, or other network, and regardless of whether satellite signal reception, assistance data reception, and/or position-related processing occurs at the device, at a server computer, or at another device associated with the network. Any operable combination of the above are also considered a "mobile station." The terms "mobile station" and "mobile device" are often used interchangeably. Personal Information Managers (PIMs) and Personal Digital Assistants (PDAs) which are capable of receiving wireless communications. Note that in some aspects of the described implementations, such a mobile station is equipped with a network listening module (NLM) configured to use PRS signals to perform TOA measurements that are then transmitted to a location computer (not shown).

The methodologies described herein in reference to any one or more of FIGS. 3E, 3F, 4A, 4B, 4C and 4D may be implemented by various means depending upon the application. For example, these methodologies may be implemented in hardware, firmware, software, or a combination thereof. For a hardware implementation, one or more processing units, such as processor 506 (FIG. 5) of computer 500 may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any non-transitory machine readable medium tangibly embodying instructions (e.g. in binary) may be used in implementing the methodologies described herein. For example, computer instructions (in the form of software) may be stored in a memory 505 (FIG. 5) of computer 500, and executed by a processor 506, for example a microprocessor. Memory 505 (FIG. 5) may be implemented within a single chip that includes processor 506 or external to the chip that contains processor 506. As used herein the term "memory" refers to any type of long term, short term, volatile (e.g. DRAM), nonvolatile (e.g. SRAM), or other memory accessible by processor 506, and is not to be limited to any particular type of memory or number of memories, or type of media upon which memory is stored.

As noted above, electronic devices 101, 102, 104, 106 may include one or more processors and one or more memories, similar or identical to computer 500, including processor(s) 506 and memory 505 that contains software in the form of instructions executable by processor(s) 506. Hence, such processor(s) 506 (FIG. 5) may be programmed with instructions comprised in non-transitory computer-readable storage media, to prepare and transmit measurements of an AC electrical signal that have been stored in non-volatile memory 314 (FIG. 3C) by analog-to-digital converter 313.

Memory 505 may include instructions 510 to processor 506 to use AC electrical signal measurements to train a classifier 521 in one or more training phases, and to operate the classifier 521 in normal operation. Instructions 510 may include, for example, a first sequence of instructions to signal AC receiving circuitry 320 (FIG. 3C) to measure, at multiple frequencies, a property of an AC signal propagating through body 100, to obtain a set of measurements, wherein the property depends at least on a frequency of the AC signal. Moreover, instructions 510 may include, for example, a second sequence of instructions to configure sensor(s) 332, at least based on a predetermined pair of locations on body 100 at which are located the electronic device 102 (FIG. 3C) and an electronic device 101 that transmits the AC signal (FIG. 3B).

Also, instructions 510 may include instructions to operate classifier 521, to select a predetermined pair of locations based on the set of measurements, from among a plurality of predetermined pairs of locations possible for the electronic device 101 and the electronic device 102. Classifier 521 may be implemented by software in memory 505 in the form of one or more additional sequence(s) of instructions which are executed by processor 506, and/or classifier 521 may be implemented in special-purpose hardware, e.g. as one or more application specific integrated circuits (ASICs), digital signal processors (DSPs), digital signal processing devices (DSPDs), programmable logic devices (PLDs), field programmable gate arrays (FPGAs), depending on the implementation. If implemented in firmware and/or software, a classifier 521 may be stored as instructions or code on a non-transitory computer-readable storage medium. Examples include non-transitory computer-readable storage media encoded with a data structure and non-transitory computer-readable storage media encoded with a computer program.

Non-transitory computer-readable storage media may take the form of an article of manufacture. Non-transitory computer-readable storage media includes any physical computer storage media that can be accessed by a computer. By way of example, and not limitation, such non-transitory computer-readable storage media can comprise SRAM, ROM, EEPROM, CD-ROM or other optical disk storage, magnetic disk storage or other magnetic storage devices, or any other non-transitory medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

In some implementations, AC receiving circuitry 320 of the type illustrated in FIG. 3C implements means for measuring, at multiple frequencies, a property of an AC signal propagating through body 100, to obtain a set of measurements, wherein the property depends at least on a frequency of the AC signal. In such implementations, the set of measurements may be supplied by the AC receiving circuitry 320 to computer 500. In computer 500, a sequence of instructions in memory 505 may be executed by processor 506 (FIG. 5), on the set of measurements, to implement means for configuring sensor(s) 332 (FIG. 3C), at least based on the predetermined pair of locations on body 100 at which are located an apparatus that contains AC receiving circuitry 320, and an electronic device 101 that transmits the AC signal, wherein the predetermined pair of locations are selectable based on the set of measurements, from among a plurality of predetermined pairs of locations possible for the electronic device 101 and the apparatus.

In addition to using AC electrical signal measurements made by analog-to-digital converter 313 as noted above, computer 500 may be configured to use other location determination methods such as Global Positioning System (GPS), and/or various other satellite positioning systems (SPS), such as the Russian Glonass system, the European Galileo system, any system that uses satellites from a combination of satellite systems, or any satellite system developed in the future. Furthermore, some aspects of the disclosed method and apparatus may be used by computer 500 with positioning determination systems that utilize wireless signals from pseudolites or a combination of satellites and pseudolites. Pseudolites are ground-based transmitters that broadcast a PN code or other ranging code (similar to a GPS or CDMA cellular signal) modulated on an L-band (or other frequency) carrier signal, which may be synchronized with GPS time. Moreover, position determination techniques used by computer 500 may be used for various wireless communication networks such as a wireless wide area network (WWAN), a wireless local area network (WLAN), a wireless personal area network (WPAN), and so on.

The term "network" and "system" are often used interchangeably. A WLAN may be an IEEE 802.11x network, and a WPAN may be a Bluetooth network, an IEEE 802.15x, or some other type of network. The techniques may also be used for any combination of WWAN, WLAN and/or WPAN. The described implementations may be implemented in conjunction with Wi-Fi/WLAN or other wireless or wired networks by use of a transmitter 502 (FIG. 5) and a receiver 503 that transmit and receive signals to/from electronic devices 101, 102 (e.g. measurements of AC signals, after passage through a body) either wirelessly or via wire(s). Computer 500 includes a clock 507 that is coupled to processor 506, transmitter 502, and receiver 503 in a normal manner. Computer 500 may optionally include a display 511 and/or a keypad 512 that may be coupled to processor 506 in a normal manner, to receive user input (e.g. strings of characters that form labels of locations on body 100, at which electronic devices 101, 102, 104, 106 and/or 111 have been placed).

This disclosure includes example implementations; however, other implementations can be used. Designation that something is "optimized," "required" or other designation does not indicate that the current disclosure applies only to systems that are optimized, or systems in which the "required" elements are present (or other limitation due to other designations). These designations refer only to the particular described implementation.

Of course, many implementations of a method and system described herein are possible depending on the aspect of the described implementations. The techniques can be used with protocols other than those discussed herein, including protocols that are in development or to be developed.

"Instructions" as referred to herein include expressions which represent one or more logical operations. For example, instructions may be "machine-readable" by being interpretable by a machine (in one or more processors) for executing one or more operations on one or more data objects. However, this is merely an example of instructions and claimed subject matter is not limited in this respect. In another example, instructions as referred to herein may relate to encoded commands which are executable by a processing circuit (or processor, e.g. processor(s) 506) having a command set which includes the encoded commands. Such an instruction may be encoded in the form of a machine language understood by the processing circuit. Again, these are merely examples of an instruction and claimed subject matter is not limited in this respect.

In several aspects of the described implementations, a non-transitory computer-readable storage medium (such as non-volatile memory 314) is capable of maintaining measurements (e.g. made by analog-to-digital converter 313), which are perceivable by one or more machines. For example, a non-transitory computer-readable storage medium may comprise one or more storage devices for storing machine-readable instructions and/or information. Such storage devices may comprise any one of several non-transitory storage media types including, for example, magnetic, optical or semiconductor storage media. Such storage devices may also comprise any type of long term, short term, volatile or non-volatile devices, and/or memory devices. However, these are merely examples of a non-volatile computer-readable storage medium and claimed subject matter is not limited in these respects.

Unless specifically stated otherwise, as apparent from the following discussion, it is appreciated that throughout this specification discussions utilizing terms such as "processing," "computing," "calculating," "selecting," "forming," "enabling," "inhibiting," "locating," "terminating," "identifying," "initiating," "detecting," "solving", "obtaining," "hosting," "maintaining," "representing," "estimating," "reducing," "associating," "receiving," "transmitting," "determining," "storing" and/or the like refer to the actions and/or processes that may be performed by a computing platform, such as a computer or a similar electronic computing device, that manipulates and/or transforms data represented as physical electronic and/or magnetic quantities and/or other physical quantities within the computing platform's processors, memories, registers, and/or other information storage, transmission, reception and/or display devices. Such actions and/or processes may be executed by a computing platform under the control of machine (or computer) readable instructions stored in a non-transitory computer-readable storage medium, for example. Such machine (or computer) readable instructions may comprise, for example, software or firmware stored in a non-transitory computer-readable storage medium included as part of a computing platform (e.g., included as part of a processing circuit or external to such a processing circuit). Further, unless specifically stated otherwise, a process described herein, with reference to flow diagrams or otherwise, may also be executed and/or controlled, in whole or in part, by such a computing platform.

Various adaptations and modifications may be made without departing from the scope of the described implementations. Numerous modifications and adaptations of the implementations described herein are encompassed by the attached claims.

The invention claimed is:

1. A method to operate a first electronic device located on a body of a human or an animal, the method comprising:
   measuring within the first electronic device, at a plurality of frequencies, a property of an intrabody AC electrical signal propagating from a second electronic device through at least one of skin, tissue or organs of the body to the first electronic device, to obtain a new profile comprising a plurality of measurements corresponding to the plurality of frequencies;
   wherein the property depends at least on a frequency of the intrabody AC electrical signal;
   selecting from among multiple predetermined pairs of body locations, a particular predetermined pair of body locations, based on determining that among multiple known profiles corresponding to the multiple predetermined pairs of body locations, a particular known profile matches the new profile, the particular known profile corresponding to the particular predetermined pair of body locations;
   wherein the multiple known profiles are stored in memory before the measuring, at least based on additional measurements of the property of the intrabody AC electrical signal during propagation between each pair in the multiple predetermined pairs of body locations; and
   configuring the first electronic device, at least based on the particular predetermined pair of body locations selected by the selecting.

2. The method of claim 1 wherein:
   the predetermined pair of locations is selected by use of a classifier that comprises a neural network, the classifier having been trained on the multiple known profiles corresponding to the multiple predetermined pairs of body locations, each known profile corresponding to one predetermined pair of body locations.

3. The method of claim 2 wherein
   the multiple predetermined pairs of body locations comprise a group of predetermined pairs of body locations, such that one body location in each predetermined pair of body locations in the group is a common known location;
   the second electronic device, which transmits the intrabody AC electrical signal, is located on the body, at the common known location; and
   the additional measurements are made in a group of electronic devices including the first electronic device which receive the intrabody AC electrical signal, the group of electronic devices being located at other body locations in each predetermined pair of body locations.

4. The method of claim 1 wherein said configuring comprises turning on or turning off a sensor that measures a specific property of the body, the sensor being comprised in the first electronic device.

5. The method of claim 1 wherein said configuring comprises setting a threshold for counting a step in an activity sensor comprised in the first electronic device.

6. The method of claim 1 wherein said configuring comprises setting a rate of transmission of data from the first electronic device depending on a specific predetermined body location in the particular predetermined pair of body locations at which the first electronic device is identified as being attached to the body by said configuring.

7. The method of claim 1 wherein said property is a specific attribute of a scattering parameter of an electrical network formed by the first electronic device and the second electronic device with the body, wherein the specific attribute is one of amplitude or phase.

8. The method of claim 7 wherein the scattering parameter is the parameter $S_{21}$.

9. The method of claim 1 wherein:
   the first electronic device and the second electronic device are identical;
   the first electronic device and the second electronic device are comprised in a number X of electronic devices on the body; and
   a number Y of the plurality of predetermined pairs of locations is determined by $Y=0.5X(X-1)$.

10. A non-transitory computer-readable storage media comprising a plurality of instructions, which, when executed by a processor perform steps in a method to operate a first electronic device located on a body of a human or an animal, the plurality of instructions comprising:
    instructions to signal the first electronic device to measure, at a plurality of frequencies, a property of an intrabody AC electrical signal propagating from a second electronic device through at least one of skin, tissue or organs of the body to the first electronic device, to obtain a new profile comprising a plurality of measurements corresponding to the plurality of frequencies;
    wherein the property depends at least on a frequency of the intrabody AC electrical signal;
    instructions to select from among multiple predetermined pairs of body locations, a particular predetermined pair of body locations, based on determining that among multiple known profiles corresponding to the multiple predetermined pairs of body locations, a particular known profile matches the new profile, the particular known profile corresponding to the particular predetermined pair of body locations;
    wherein the multiple known profiles are stored in memory before execution of the instructions to signal, at least based on additional measurements of the property of the intrabody AC electrical signal during propagation between each pair in the multiple predetermined pairs of body locations; and
    instructions to configure the first electronic device, at least based on the particular predetermined pair of body locations selected by execution of the instruction to select.

11. The non-transitory computer-readable storage media of claim 10 wherein:
    the predetermined pair of locations is selected by use of a classifier that comprises a neural network, the classifier having been trained on the multiple known profiles corresponding to the multiple predetermined pairs of body locations, each known profile corresponding to one predetermined pair of body locations.

12. The non-transitory computer-readable storage media as recited in claim 11 wherein:
    the multiple predetermined pairs of body locations comprise a group of predetermined pairs of body locations, such that one body location in each predetermined pair of body locations in the group is a common known location;
    the second electronic device, which transmits the intrabody AC electrical signal, is located on the body, at the common known location; and
    the additional measurements are made in a group of electronic devices including the first electronic device which receive the intrabody AC electrical signal, the group of electronic devices being located at other body locations in each predetermined pair of body locations.

13. The non-transitory computer-readable storage media of claim 10 wherein said instructions to configure comprise instructions to turn on or turn off a specific sensor that measures a specific property of the body, the sensor being comprised in the first electronic device.

14. The non-transitory computer-readable storage media of claim 10 wherein said instruction to configure comprise instructions to set a threshold of a for counting a step in an activity sensor comprised in the first electronic device.

15. The non-transitory computer-readable storage media of claim 10 wherein said instructions to configure comprise instructions to set a rate of transmission of data from the first electronic device depending on a specific predetermined body location in the particular predetermined pair of body locations at which the first electronic device is identified as being attached to the body by execution of the instructions to configure.

16. The non-transitory computer-readable storage media of claim 10 wherein said property is a specific attribute of a scattering parameter of an electrical network formed by the first electronic device and the second electronic device with the body, wherein the specific attribute is one of amplitude or phase.

17. The non-transitory computer-readable storage media of claim 16 wherein the scattering parameter is the parameter $S_{21}$.

18. The non-transitory computer-readable storage media of claim 10 wherein:
the first electronic device and the second electronic device are identical;
the first electronic device and the second electronic device are comprised in a number X of electronic devices on the body; and
a number Y of the plurality of predetermined pairs of locations is determined by $Y=0.5X(X-1)$.

19. An electronic device comprising:
circuitry to measure an intrabody AC electrical signal;
a sensor;
a memory;
a processor operatively connected to the memory to execute a plurality of instructions stored in the memory, the processor being coupled to the circuitry and the sensor;
the plurality of instructions comprising:
instructions to signal the circuitry to measure at a plurality of frequencies, a property of the intrabody AC electrical signal received at the circuitry through at least one of skin, tissue or organs of the body, to obtain a plurality of measurements corresponding to the plurality of frequencies;
wherein the property depends at least on a frequency of the intrabody AC electrical signal;
instructions to select from among multiple predetermined pairs of body locations, a particular predetermined pair of body locations, based on determining that among multiple known profiles corresponding to the multiple predetermined pairs of body locations, a particular known profile matches the new profile, the particular known profile corresponding to the particular predetermined pair of body locations;
wherein the multiple known profiles are stored in memory before execution of the instructions to signal, at least based on additional measurements of the property of the intrabody AC electrical signal during propagation between each pair in the multiple predetermined pairs of body locations; and
instructions to configure the sensor, at least based on the particular predetermined pair of body locations selected by execution of the instruction to select.

20. The electronic device of claim 19 wherein:
the predetermined pair of locations is selected by use of a classifier that comprises a neural network, the classifier having been trained on the multiple known profiles corresponding to the multiple predetermined pairs of body locations, each known profile corresponding to one predetermined pair of body locations.

21. The electronic device of claim 19 wherein:
the multiple predetermined pairs of body locations comprise a group of predetermined pairs of body locations, such that one body location in each predetermined pair of body locations in the group is a common known location; and
another electronic device, which transmits the intrabody AC electrical signal, is located on the body, at the common known location.

22. The electronic device of claim 19 further comprising a transmitter, wherein instructions to configure comprise instructions to set a rate of transmission of data by the transmitter depending on a specific predetermined body location in the particular predetermined pair of body locations at which the electronic device is identified as being attached to the body by execution of the instructions to configure.

23. The electronic device of claim 19 wherein said property is a specific attribute of a scattering parameter of an electrical network formed by the electronic device and another electronic device with the body, wherein the specific attribute is one of amplitude or phase.

24. The electronic device of claim 23 wherein the scattering parameter is the parameter $S_{21}$.

25. An apparatus comprising:
a memory;
a sensor;
a processor operatively connected to the memory to execute a plurality of instructions stored in the memory;
means for measuring, at a plurality of frequencies, a property of an intrabody AC electrical signal propagating from an electronic device through at least one of skin, tissue or organs of a body, to obtain a plurality of measurements corresponding to the plurality of frequencies;
wherein the property depends at least on a frequency of the intrabody AC electrical signal;
means for selecting from among multiple predetermined pairs of body locations, a particular predetermined pair of body locations, based on determining that among multiple known profiles corresponding to the multiple predetermined pairs of body locations, a particular known profile matches the new profile, the particular known profile corresponding to the particular predetermined pair of body locations;
wherein the multiple known profiles are stored in memory before operation of the means for measuring, at least based on additional measurements of the property of the intrabody AC electrical signal during propagation between each pair in the multiple predetermined pairs of body locations; and
means for configuring the sensor, at least based on the particular predetermined pair of body locations selected by the means for selecting.

26. The apparatus of claim 25 wherein:
the predetermined pair of locations is selected by use of a classifier that comprises a neural network, the classifier having been trained on the multiple known profiles corresponding to the multiple predetermined pairs of body locations, each known profile corresponding to one predetermined pair of body locations.

27. The apparatus of claim 25 wherein:
the multiple predetermined pairs of body locations comprise a group of predetermined pairs of body locations, such that one body location in each predetermined pair of body locations in the group is a common known location; and
the electronic device, which transmits the intrabody AC electrical signal, is located on the body, at the common known location.

28. The apparatus of claim 25 further comprising means for transmission, wherein said means for configuring sets a rate of transmission of data by the means for transmission depending on a specific predetermined body location in the particular predetermined pair of body locations at which the electronic device is identified as being attached to the body by said means for configuring.

29. The apparatus of claim 25 wherein said property is a specific attribute of a scattering parameter of an electrical network formed by the apparatus and the electronic device with the body, wherein the specific attribute is one of amplitude or phase.

30. The apparatus of claim 25 wherein the scattering parameter is the parameter $S_{21}$.

* * * * *